United States Patent [19]

Stowasser et al.

[11] Patent Number: 5,663,139

[45] Date of Patent: Sep. 2, 1997

[54] INHIBITORS OF RETROVIRAL PROTEASES

[75] Inventors: Bernd Stowasser, Gross-Umstadt, Germany; Jian-Qi Li, Shanghai, China; Anuschirwan Peyman; Karl-Heinz Budt, both of Kelkheim/Taunus, Germany

[73] Assignee: Hoechst Aktiengesellschaft, Frankfurt am Main, Germany

[21] Appl. No.: 360,662

[22] PCT Filed: Jun. 22, 1993

[86] PCT No.: PCT/EP93/01594

§ 371 Date: Dec. 22, 1994

§ 102(e) Date: Dec. 22, 1994

[87] PCT Pub. No.: WO94/00461

PCT Pub. Date: Jan. 6, 1994

[30] Foreign Application Priority Data

Jun. 24, 1992 [DE] Germany ............... 42 20 566.2

[51] Int. Cl.$^6$ ............... A61K 38/07; A61K 38/08; C07K 5/10
[52] U.S. Cl. ............... 514/7; 514/18; 530/323; 530/330; 530/331
[58] Field of Search ............... 530/331, 330, 530/323; 514/18, 7

[56] References Cited

FOREIGN PATENT DOCUMENTS 2 032 303   6/1991   Canada .
0 428 849   5/1991   European Pat. Off. .

OTHER PUBLICATIONS

Fox, J.L., "No winners against AIDS", Bio/Technology, vol. 12, p. 128. Feb. 1994.

I. Katoh et al., Nature, "Inhibition Of Retroviral Protease Activity By An Aspartyl Proteinase Inhibitor", vol. 329, No. 6140, pp. 654–656, Oct., 1987.

Stowasser et al. Tetrahedron Lett. vol. 33 No. 44 pp. 6625–6628 (Oct. 27, 1992).

Primary Examiner—Cecilia J. Tsang
Assistant Examiner—Anish Gupta
Attorney, Agent, or Firm—Finnegan, Henderson, Farabow, Garrett & Dunner, L.L.P.

[57] ABSTRACT

The present invention relates to a compound of the formula

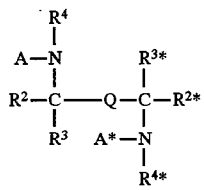

in which

A, Q, $R^2$, $R^3$ and $R^4$, and also the corresponding, asterisked radicals, are defined as indicated in the description, to a process for their preparation, and also to their use for inhibiting retroviral proteases.

10 Claims, No Drawings

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Ser Phe Asn Phe Pro Gln Ile
    1                 5

( 2 ) INFORMATION FOR SEQ ID NO:2:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide (ix) FEATURE:
    (A) NAME/KEY: Peptide
    (B) LOCATION: 5
    (D) OTHER INFORMATION: /note= "Xaa = 5 oxaproline."

(xi) SEQUENCE DESCRIPTION: SEQ ID NO:2:

Ser Phe Asn Phe Xaa Gln Ile
1               5

INHIBITORS OF RETROVIRAL PROTEASES

The present invention relates to substances which inhibit the action of retroviral proteases, to a process for their preparation and to their use, and also to pharmaceuticals containing these substances.

The etiological cause of acquired immune deficiency syndrome (AIDS) is the so-called human immunodeficiency virus (HIV) (F. Barre-Sinoussi et al., Science 220, (1983), 868–870; R. C. Gallo et al., Science 224, (1984), 500–502; R. C. Gallo and L. Montagnier, Scient. Am. 259(4), (1988), 40–48). HIV is a retrovirus and is included in the lentivirus group (M. A. Gonda, F. Wong-Staal and R. C. Gallo, Science, 227, (1985), 173; P. Sonigo et al., Cell, 42, (1985), 369).

The AIDS epidemic has by now spread, to a greater or lesser extent, to virtually all countries. The World Health Organization (WHO) estimates the number of infected adults worldwide to be about 8–10 million (Weekly Epidemiological Record, World Health Organization, Geneva, 1991, 66, 353–357). Of these, more than 1 million already have AIDS and a further million have developed serious infection-related diseases. 1 million children have been born who have been infected by their mothers and, of these children, about half have already developed AIDS or have died. WHO calculates that in the year 2000 roughly 30–40 million people will be infected.

While the sole substance hitherto licensed for the indication AIDS, zidovudine (AZT), is able to prolong patient life in many cases, it possesses serious, toxic side effects which in many cases require therapy to be discontinued. Strains of HIV have already been discovered which exhibited significantly less sensitivity to AZT and thus gave rise to the development of resistance. Further approaches to HIV therapy are therefore urgently required.

In analogy with proteins of other retroviruses, HIV proteins are initially translated as long, precursor gag, pol and env polyproteins (C. Dickson et al., in RNA Tumor Viruses (Editors: R. Weiss, N. Teich, H. Varmus and J. Coffin) 2nd Ed., revised, pages 513–648, Cold Spring Harbor Laboratory, Cold Spring Harbor, N.Y.) and are only subsequently processed proteolytically to form the structural proteins (p17 (MA), p24 (CA), p7 (NC) and p6), the enzymes (protease (PR), reverse transcriptase (RT) and integrase (IN)), and the coat proteins (gp120 (SU) and gp41 (TM)) (Nomenclature: J. Leis et al., J. Virol. 62, (1988), (1808–1809)). It is assumed that the cleavage of the gag and pol polyproteins is brought about by a virally encoded protease. Mutations within the region encoding the protease give rise to non-infectious virus particles (N. E. Kohl et al. Proc. Natl. Acad. Sci. USA 85, (1988), (4686–4690)).

The HIV protease is composed of 99 amino acids and evidently excises itself out of the pol polyprotein by hydrolyzing the two Phe-Pro bonds in positions 68–69 and 167–168, respectively (M. C. Graves, J. J. Lim, E. P. Heimer and R. A. Kramer Proc. Natl. Acad. Sci. USA 85 (1988); 2449–2453; J. Hansen, S. Billich, T. Schulze, S. Sukrow and K. Mölling, EMBO J. 7 (1988), 1785–1791; E. P. Lillehoj et al., J. Virology 62 (1988) 3053–3058; J. Schneider and S. B. H. Kent, Cell 54 (1988) 363–368).

Some inhibitors of the HIV protease are already known from the literature. The first representative was pepstatin A, which has an $IC_{50}$ value of approximately 0.5 mmol/l (I. Katoh, T. Yasunaga, Y. Ikawa and Y. Yoshinaka, Nature, 329, (1987), 654–656). Since then, some other inhibitors have been described (see, for example, B. A. G. Tomaselli et al., Chim. Oggi 9(5), (1991), 6027, EP 0428849, EP 0435059).

A novel structural class has now been found which is highly active in inhibiting the HIV protease in an enzyme test.

The present invention relates to compounds of the formula

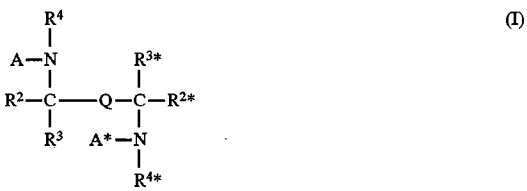

c1.1) in which

Q is a radical of the formula IIa or IIb

Y is oxygen or sulfur, and

A is a radical of the formula IV and A* is a radical of the formula IV*,

where

E, E*, F, F*, G and G*, independently of each other, are a natural or unnatural amino acid, azaamino acid or imino acid;

n, n*, o, o*, p and p*, independently of each other, are 0 or 1;

D is $R^1$ or a radical of the formulae V, VI or VII, and

D* is $R^{1*}$ or a radical of the formulae V*, VI* or VII*,

and in which $R^1$ and $R^{1*}$, independently of each other, a1) are hydrogen, carboxyl,
(C$_1$–C$_{18}$)-alkyl, which is optionally unsaturated once or twice and which is optionally substituted by up to 3 identical or different radicals from the group
mercapto,
hydroxyl,
(C$_1$–C$_7$)-alkoxy,
carbamoyl,
(C$_1$–C$_8$)-alkanoyloxy,
carboxyl,
(C$_1$–C$_7$)-alkoxycarbonyl,
F, Cl, Br, I,
amino,
amidino, which can be optionally substituted by one, two or three (C$_1$–C$_8$)-alkyl radicals,
guanidino, which can be optionally substituted by one or two benzyloxycarbonyl radicals or by one, two, three or four (C$_1$–C$_8$)-alkyl radicals,
(C$_1$–C$_7$)-alkylamino,
di-(C$_1$–C$_7$)-alkylamino,
(C$_1$–C$_6$)-alkoxycarbonylamino,
(C$_7$–C$_{15}$)-aralkoxycarbonyl,
(C$_7$–C$_{15}$)-aralkoxycarbonylamino,
phenyl-(C$_1$–C$_4$)-alkoxy,
9-fluorenylmethoxycarbonylamino,
(C$_1$–C$_6$)-alkylsulfonyl,
(C$_1$–C$_6$)-alkylsulfinyl,
(C$_1$–C$_6$)-alkylthio,
hydroxyamino,
hydroxyimino,
sulfamoyl,
sulfo,
carboxamido,
formyl,
hydrazono,
imino,
phenyl,
a radical CONR$^{12}$R$^{13}$ or CONR$^{12}$*R$^{13}$*,
by up to six hydroxyl, or
by up to five (C$_1$–C$_8$)-alkanoyloxy;
monocyclic, bicyclic or tricyclic (C$_3$–C$_{18}$)-cycloalkyl, (C$_3$—C$_{18}$)-cycloalkyl-(C$_1$–C$_6$)-alkyl
where the cycloalkyl moiety is in each case optionally substituted by one or two identical or different radicals from the group
F, Cl, Br, I,
carboxyl,
carbamoyl,
carboxymethoxy,
hydroxyl,
(C$_1$–C$_7$)-alkoxy,
(C$_1$–C$_7$)-alkyl,
(C$_1$–C$_7$)-alkyloxycarbonyl,
amino,
(C$_1$–C$_6$)-alkylamino-(C$_1$–C$_6$)-alkyl,
di-(C$_1$–C$_6$)-alkylamino-(C$_1$–C$_6$)-alkyl,
amidino,
hydroxyamino,
hydroxyimino,
hydrazono,
imino,
guanidino,
(C$_1$–C$_6$)-alkoxysulfonyl,
(C$_1$–C$_6$)-alkoxysulfinyl,
(C$_1$–C$_6$)-alkoxycarbonylamino,
(C$_6$–C$_{12}$)-aryl-(C$_1$–C$_4$)-alkoxycarbonylamino,
(C$_1$–C$_7$)-alkylamino,
di-(C$_1$–C$_7$)-alkylamino, and
trifluoromethyl;
(C$_6$–C$_{14}$)-aryloxy-(C$_1$–C$_6$)-alkyl,
(C$_6$–C$_{14}$)-aryl,
(C$_6$–C$_{14}$)-aryl-(C$_1$–C$_6$)-alkyl, or
(C$_6$–C$_{14}$)-aryl-(C$_3$–C$_8$)-cycloalkyl, in which the aryl moiety is in each case optionally substituted by one, two or three identical or different radicals from the group
F, Cl, Br, I,
hydroxyl,
mono-, di- or trihydroxy-(C$_1$–C$_4$)-alkyl,
trifluoromethyl,
formyl,
carboxamido,
mono- or di-(C$_1$–C$_4$)-alkylaminocarbonyl,
nitro,
(C$_1$–C$_7$)-alkoxy,
(C$_1$–C$_7$)-alkyl,
(C$_1$–C$_7$)-alkoxycarbonyl,
amino,
(C$_1$–C$_7$)-alkylamino,
di-(C$_1$–C$_7$)-alkylamino,
carboxyl,
carboxymethoxy,
amino-(C$_1$–C$_7$)-alkyl,
(C$_1$–C$_7$)-alkylamino-(C$_1$–C$_7$)-alkyl,
di-(C$_1$–C$_7$)-alkylamino-(C$_1$–C$_7$)-alkyl,
(C$_1$–C$_7$)-alkoxycarbonylmethoxy,
carbamoyl,
sulfamoyl,
(C$_1$–C$_7$)-alkoxysulfonyl,
(C$_1$–C$_8$)-alkylsulfonyl,
sulfo-(C$_1$–C$_8$)-alkyl,
guanidino-(C$_1$–C$_8$)-alkyl and
(C$_1$–C$_6$)-alkoxycarbonylamino;
Het,
Het-(C$_1$–C$_6$)-alkyl,
Het-(C$_3$–C$_8$)-cycloalkyl,
Het-(C$_3$–C$_8$)-cycloalkyl-(C$_1$–C$_4$)-alkyl,
Het-(C$_3$–C$_8$)-cycloalkoxy-(C$_1$–C$_4$)-alkyl,
Het-thio-(C$_1$–C$_6$)-alkyl,
Het-thio-(C$_3$–C$_8$)-cycloalkyl,
Het-thio-(C$_3$–C$_8$)-cycloalkyl-(C$_1$–C$_4$)-alkyl, where Het is in each case the radical of a 5- to 7-membered monocyclic or 8- to 10-membered bicyclic ring system which can be benzofused, aromatic, partially hydrogenated or completely hydrogenated, which can contain, as heteroelements, one, two, three or four different radicals from the group N, O, S, NO, SO, and SO$_2$, which can be substituted by 1 to 6 hydroxyl and which is optionally monosubstituted, disubstituted or trisubstituted as defined for (C$_6$–C$_{14}$)-aryl under a1) and/or by oxo, or are a radical NR$^{12}$R$^{13}$ or NR$^{12}$*R$^{13}$*, respectively, or, a2) are a radical of the formula VIII or VIII*, respectively, $$R1a-W \qquad\qquad (VIII)$$

$$R1a*-W \qquad\qquad (VIII*)$$

in which R1a and R1a* are defined as are R1 and R1*, respectively, under a1) and W or W* is —CO—, —CS—, O—CO—, —SO$_2$—, —SO—, —S—, —NHSO$_2$—, —NHCO—, —CH(OH)—, —N(OH)— or —CO—V—, where V is a peptide having from 1 to 10 amino acids;

or in which $R^1$ and $R^{1*}$, independently of each other, form, together with $R^{11}$ or $R^{11*}$, respectively, and the atoms carrying the latter, monocyclic or bicyclic, saturated or partially unsaturated, ring systems having 5–12 ring members which, in addition to carbon, can also contain 1 sulfur atom which can optionally be oxidized to the sulfoxide or sulfone;

a3)
are a glycosyl radical, preferably a glucofuranosyl or glucopyranosyl radical, which is derived from naturally occurring aldotetroses, aldopentoses, aldohexoses, ketopentoses, ketohexoses, deoxyaldoses, aminoaldoses and oligosaccharides and also their stereoisomers;

$R^2$ and $R^{2*}$,
independently of each other, are defined as are $R^1$ and $R^{1*}$, respectively, under a1) or a2), or form, together with $R^4$ or $R^{4*}$, respectively, and the atoms carrying the latter, monocyclic or bicyclic, saturated or partially unsaturated, ring systems having from 5 to 12 ring members, or form, together with $R^3$ or $R^{3*}$, respectively, and the atoms carrying the latter, cyclic, saturated or partially unsaturated, ring systems having from 3 to 12 ring members;

$R^3$ and $R^{3*}$, independently of each other, are
hydrogen or
$(C_1-C_3)$-alkyl;

$R^4$ and $R^{4*}$, independently of each other, are
hydrogen or
$(C_1-C_8)$-alkyl;

$R^5$ is
hydrogen,
$(C_1-C_{20})$-alkyl,
$(C_2-C_{20})$-alkenyl or alkynyl,
$(C_7-C_{20})$-arylalkyl or $(C_6-C_{20})$-aryl,
$(C_3-C_8)$-cycloalkyl which can be optionally substituted by different radicals from the group hydroxyl, alkoxy, carboxyl, alkanoyloxy, alkoxycarbonyl, F, Cl, Br, I, amino, alkylamino or dialkylamino;
an equivalent of a pharmaceutically tolerated cation,
or
is a phosphinate prodrug;

$R^6$ is oxygen or sulfur;

$R^7$ and $R^{7*}$, independently of each other, are
hydrogen,
$(C_1-C_{20})$-alkyl,
$(C_2-C_{20})$-alkenyl or alkynyl, $(C_6-C_{20})$-aryl,
$(C_7-C_{20})$-arylalkyl, which can be optionally substituted by different radicals from the group hydroxyl, alkoxy, carboxyl, alkanoyloxy, alkoxycarbonyl, F, Cl, Br, I, amino, alkylamino or dialkylamino,
or, together, can form a ring having 2–6 carbon atoms, $R^8$ and $R^{8*}$, independently of each other, are
hydrogen or
$(C_1-C_8)$-alkyl, or,
together with $R^9$ or $R^{9*}$, respectively, and the atoms carrying the latter, form monocyclic or bicyclic, saturated or partially unsaturated, ring systems having 5–12 ring members;

$R^9$ and $R^{9*}$
are, independently of each other, defined as are $R^1$ and $R^{1*}$, respectively, under a1), are hydroxyl or $(C_1-C_8)$-alkanoyloxy, or form, together with $R^{10}$ or $R^{10*}$, respectively, and the atoms carrying the latter, cyclic, saturated or partially unsaturated, ring systems having from 3 to 12 ring members;

or
form, together with $R^{11}$ or $R^{11*}$, respectively, and the atoms carrying the latter, a monocyclic or bicyclic, saturated or partially unsaturated, ring system having 5–12 ring members which, in addition to carbon, can also contain 1 sulfur atom which can optionally be oxidized to the sulfoxide or sulfone; or can contain 1 nitrogen atom, where the ring system can optionally be substituted by amino;

$R^{10}$ and $R^{10*}$, independently of each other, are
hydrogen or
$(C_1-C_6)$-alkyl;

$R^{11}$ and $R^{11*}$, independently of each other, are
hydrogen,
hydroxyl,
$(C_1-C_4)$-alkanoyloxy, or
$(C_1-C_8)$-alkyl;

$R^{12}$, $R^{12*}$, $R^{13}$ and $R^{13*}$, independently of each other, are
hydrogen,
$(C_1-C_8)$-alkyl which can be substituted by
amino,
$(C_1-C_4)$-alkylamino,
di-$(C_1-C_4)$-alkylamino,
mercapto,
carboxyl,
hydroxyl or
$(C_1-C_4)$-alkoxy,
$(C_3-C_7)$-cycloalkyl,
$(C_1-C_4)$-alkoxycarbonyl,
$(C_6-C_{14})$-aryl, $(C_6-C_{14})$-aryl-$(C_1-C_4)$-alkoxycarbonyl which can be substituted in the aryl moiety as described for $R^1$ or $R^{1*}$,
Het or
Het-$(C_1-C_4)$-alkyl, where Het is defined as described for $R^1$ or $R^{1*}$,
or where $R^{12}$ and $R^{13}$ or $R^{12*}$ and $R^{13*}$, respectively, form, together with the nitrogen atoms carrying them, monocyclic or bicyclic, saturated, partially unsaturated or aromatic ring systems which also contain, as further ring members in addition to carbon, 1 or 2 nitrogen atoms, 1 sulfur atom or 1 oxygen atom, and which can be substituted by $(C_1-C_4)$-alkyl, where
in the above compounds of the formula I, one or more amide groups (—CONH—) of the main chain can be replaced by —CH$_2$NR$^{14}$—, —CH$_2$S—, —CH$_2$O—, —OCH$_2$—, —CH$_2$CH$_2$—, —CH=CH— (cis and trans), —COCH$_2$—, —CH(OH)CH$_2$—, —CH$_2$SO—, —CH$_2$SO$_2$—, —COO—, —P(O)(OR$^{15}$)CH$_2$— and —P(O)(OR$^{15}$)NH—, or even by an amide group having reverse polarity (—NHCO—);

in which $R^{14}$ and $R^{15}$, independently of each other, are
hydrogen or
$(C_1-C_4)$-alkyl;
and the physiologically tolerated salts thereof.

The nomenclature employed in this description follows general practice in the case of amino acids, that is the amino group is located on the left, and the carboxyl group on the right, of each amino acid. This also applies, in a corresponding manner, for azaamino acids and imino acids.

Natural or unnatural amino acids can, if chiral, be present in the D or L form. α-Amino acids are preferred. The following may be mentioned by way of example:

Aad, Abu, γAbu, ABz, 2ABz, εAca, Ach, Acp, Adpd, Ahb, Aib, βAib, Ala, βAla, ΔAla, Alg, All, Ama, Amt, Ape, Apm, Apr, Arg, Asn, Asp, Asu, Aze, Azi, Bai, Bph, Can, Cit, Cys, (Cys)2, Cyta, Daad, Dab, Dadd, Dap, Dapm, Dasu, Djen, Dpa, Dtc, Fel, Gln, Glu, Gly, Guv, hAla, hArg, hCys, hGln, hGlu, His, hIle, hLeu, hLys, hMet, hPhe, hPro, hSer, hThr, hTrp, hTyr, Hyl, Hyp, 3Hyp, Ile, Ise, Iva, Kyn, Lant, Lcn, Leu, Lsg, Lys, βLys, ΔLys, Met, Mim, Min, nArg, Nle, Nva, Oly, Orn, Pan, Pec, Pen, Phe, Phg, Pic, Pro, ΔPro, Pse, Pya, Pyr, Pza, Qin, Ros, Sar, Sec, Sem, Ser, Thi, βThi, Thr, Thy, Thx, Tia, Tle, Tly, Trp, Trta, Tyr, Val, Nal, Tbg, Npg, Chg, Thia, (cf. e.g. Houben-Weyl, Methoden der organischen Chemie [Methods of organic chemistry], Volume XV/1 and 2, Stuttgart, 1974):

Azaamino acids are natural or unnatural amino acids where the central structural component —CHR— or $CH_2$— is replaced by —NR— or —NH—, respectively.

An imino acid is generally understood to mean a natural or unnatural amino acid whose amino group is monosubstituted. In this connection, particular mention may be made of compounds which are substituted by $(C_1-C_8)$-alkyl which, in turn, is optionally substituted as described for $C_1-C_{18}$-alkyl under a1). Heterocycles from the following group also come into consideration:

Pyrrolidine-2-carboxylic acid; piperidine-2-carboxylic acid; 1,2,3,4-tetrahydroisoquinoline-3-carboxylic acid; decahydroisoquinoline-3-carboxylic acid; octahydroindole-2-carboxylic acid; decahydroquinoline-2-carboxylic acid; octahydrocyclopenta[b]pyrrole-2-carboxylic acid; 2-azabicyclo[2.2.2]octane-3-carboxylic acid; 2-azabicyclo[2.2.1]heptane-3-carboxylic acid; 2-azabicyclo-[3.1.0]hexane-3-carboxylic acid; 2-azaspiro[4.4]nonane-3-carboxylic acid; 2-azaspiro[4.5]decane-3-carboxylic acid; spiro[(bicyclo[2.2.1]heptane)-2,3-pyrrolidine-5-carboxylic acid]; spiro[(bicyclo[2.2.2]octane)-2,3-pyrrolidine-5-carboxylic acid]; 2-azatricyclo[4.3.0.1$^{6,9}$]-decane-3-carboxylic acid; decahydrocyclohepta[b]pyrrole-2-carboxylic acid; decahydrocycloocta[b]pyrrole-2-carboxylic acid; octahydrocyclopenta[c]pyrrole-2-carboxylic acid; octahydroisoindole-1-carboxylic acid; 2,3,3a,4,6a-hexahydrocyclopenta[b]pyrrole-2-carboxylic acid; 2,3,3a,4,5,7a-hexahydroindole-2-carboxylic acid; tetrahydrothiazole-4-carboxylic acid; isoxazolidine-3-carboxylic acid; pyrazolidine-3-carboxylic acid; hydroxyproline-2-carboxylic acid; all of which can optionally be substituted by one of the following radicals:

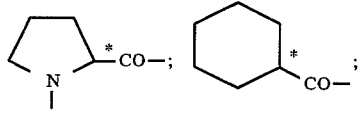

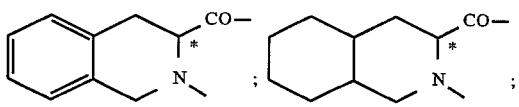

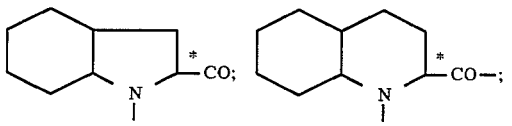

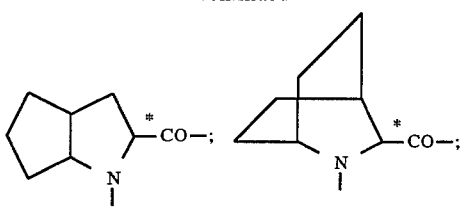

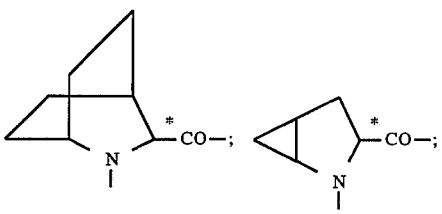

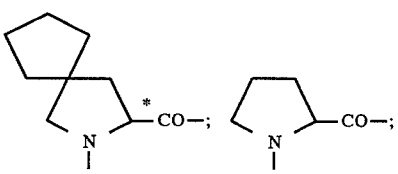

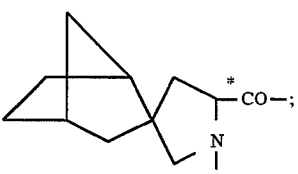

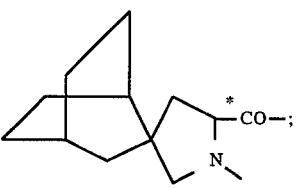

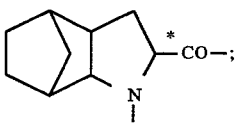

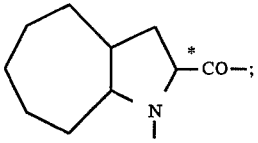

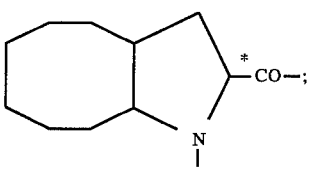

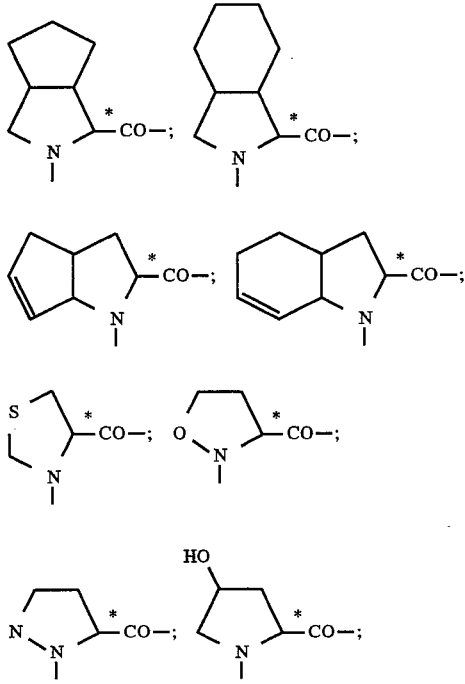

Glycosyl radicals as described above are derived, in particular, from natural D-monosaccharides or L-monosaccharides which occur in microorganisms, plants, animals or humans, such as ribose (Rib), arabinose (Ara), xylose (Xyl), lyxose (Lyx), allose (All), altrose (Alt), glucose (Glc), mannose (Man), gulose (Gul), idose (Ido), galactose (Gal), talose (Tal), erythrose (Ery), threose (Thr), psicose (Psi), fructose (Fru), sorbose (Sor), tagarose (Tag), xylulose (Xyu), fucose (Fuc), rhamnose (Rha), olivose (Oli), oliose (Olo), mycarose (Myc), rhodosamine (RN), N-acetylglucosamine (GlcNAc), N-acetylgalactosamine (GalNAc) or N-acetylmannosamine (ManNAc), or disaccharides, such as maltose (Mal), lactose (Lac), cellobiose (Cel), gentibiose (Gen), N-acetyllactosamine (LacNAc), chitobiose (Chit), β-galactopyranosyl-(1-3)-N-acetylgalactosamine and β-galactopyranosyl-(1-3)- or -(1-4)-N-acetylglucosamine, and also their synthetic derivatives, such as 2-deoxy-, 2-amino-, 2-acetamido- or 2-halo-, preferably bromo- and iodo-sugars.

The centers of chirality in the compounds of the formula (I) can have the R configuration, the S configuration or the R, S configuration.

Alkyl can be straight-chain or branched. This also applies in a corresponding manner to radicals derived from alkyl, such as, for example, alkoxy, alkylthio, alkylamino, dialkylamino, alkanoyl and aralkyl.

Cycloalkyl is also understood to mean alkyl-substituted radicals, such as, for example, 4-methylcyclohexyl or 2,3-dimethylcyclopentyl.

Bicycloalkyl or tricycloalkyl is understood to mean an isocyclic, aliphatic, non-aromatic radical which can optionally contain unsymmetrically distributed double bonds and can also optionally be substituted by open-chain aliphatic side chains. The two or three rings which are components of such a radical are fused or spiro-linked and linked via a ring C atom or a side-chain C atom. Examples of these radicals are bornyl, norbornyl, pinanyl, norpinanyl, caranyl, norcaranyl, thujanyl, adamantyl, bicyclo[3.3.0]octyl, bicyclo[4.4.0]decyl, bicyclo[1.1.0]butyl or spiro[3.3]heptyl substituents.

If the said cycles carry more than one substituent, the substituents can then be located cis or trans in relation to each other.

Examples of ($C_6$–$C_{14}$)-aryl are phenyl, naphthyl, biphenylyl or fluorenyl; phenyl and naphthyl are preferred. This also applies in a corresponding manner to radicals derived therefrom, such as, for example, aryloxy, aroyl, aralkyl and aralkoxy. Aralkyl is understood to mean an unsubstituted or substituted ($C_6$–$C_{14}$)-aryl radical which is linked to ($C_1$–$C_6$)-alkyl, such as, for example, benzyl, 1-naphthylmethyl or 2-naphthylmethyl, without, however, aralkyl being restricted to the said radicals.

Within the meaning of the above definition, Het radicals are pyrrolyl, furyl, thienyl, imidazolyl, pyrazolyl, oxazolyl, isoxazolyl, thiazolyl, isothiazolyl, tetrazolyl, pyridyl, pyrazinyl, pyrimidinyl, indolyl, isoindolyl, indazolyl, phthalazinyl, quinolyl, isoquinolyl, quinoxalinyl, quinazolinyl, cinnolinyl or β-carbolinyl, or a benzofused, cyclopenta-fused, cyclohexa-fused or cyclohepta-fused derivative of these radicals.

These heterocycles can be substituted on a nitrogen atom by oxides; ($C_1$–$C_7$)-alkyl, e.g. methyl or ethyl; phenyl; phenyl-($C_1$–$C_4$)-alkyl, e.g. benzyl; and/or on one or more carbon atoms by ($C_1$–$C_4$)-alkyl, e.g. methyl; phenyl; phenyl-($C_1$–$C_4$)-alkyl, e.g. benzyl; halogen; hydroxyl; ($C_1$–$C_4$)-alkoxy, e.g. methoxy, phenyl-($C_1$–$C_4$)-alkoxy, e.g. benzyloxy, or oxo, or be partially or completely saturated.

Examples of radicals of this type are 2- or 3-pyrrolyl; phenyl-pyrrolyl, e.g. 4- or 5-phenyl-2-pyrrolyl; 2-furyl; 2-thienyl; 4-imidazolyl; methyl-imidazolyl, e.g. 1-methyl-2-, 4- or 5-imidazolyl; 1,3-thiazol-2-yl; 2-, 3- or 4-pyridyl; 1-oxido-2-, 3- or 4-pyridino; 2-pyrazinyl; 2-, 4- or 5-pyrimidinyl; 2-, 3- or 5-indolyl; substituted 2-indolyl, e.g. 1-methyl-, 5-methyl-, 5-methoxy-, 5-benzyloxy-, 5-chloro- or 4,5-dimethyl-2-indolyl; 1-benzyl-2- or 3-indolyl; 4,5,6,7-tetrahydro-2-indolyl; cyclohepta[b]-5-pyrrolyl; 2-, 3- or 4-quinolyl; 1-, 3- or 4-isoquinolyl; 1-oxo-1,2,dihydro-3-isoquinolyl; 2-quinoxalinyl; 2-benzofuranyl; 2-benzoxazolyl; benzothiazolyl; benz[e]indol-2-yl or β-carbolin-3-yl.

Examples of partially hydrogenated or completely hydrogenated heterocyclic rings are dihydropyridinyl; pyrrolidinyl, e.g. 2-, 3- or 4-N-methylpyrrolidinyl; piperazinyl; morpholino; thiomorpholino; tetrahydrothiophenyl; benzodioxolanyl.

Halogen is fluorine, chlorine, bromine or iodine, in particular fluorine or chlorine.

Salts of compounds of the formula (I) are understood to mean, in particular, pharmaceutically utilizable or non-toxic salts.

Such salts are formed, for example, from compounds of the formula (I) which contain acidic groups, e.g. carboxyl in addition, using alkali metals or alkaline earth metals, such as, for example, Na, K, Mg and Ca, and also using physiologically tolerated organic amines, such as, for example, triethylamine and tris(2-hydroxyethyl)amine.

Compounds of the formula I which contain basic groups, e.g. an amino group or a guanadino group, form salts with inorganic acids, such as, for example, hydrochloric acid, sulfuric acid or phosphoric acid, and with organic carboxylic or sulfonic acids, such as, for example, acetic acid, citric acid, benzoic acid, maleic acid, fumaric acid, tartaric acid and p-toluenesulfonic acid.

Phosphinate prodrugs are described, for example, in H. Bundgaard, "Design of Prodrugs", Elsevier, Amsterdam 1985, pp. 70ff. Examples of such prodrug forms are glyceryl esters, 1,2-difatty acid glyceryl triesters, O-acyloxyalkyl esters and 1-methyl-2-nitroethyl esters.

Preferred pharmaceutically tolerated cations are sodium, potassium, magnesium, aluminum, lithium, ammonium and triethylammonium.

Compounds of the formula I are preferred in which, c1.2) the radicals and symbols with and without asterisk are in each case identical.

Furthermore, compounds of the formula I are particularly preferred in which, c1.3)

Q is a radical of the formulae IIa or IIb;

Y is oxygen or sulfur;

A, A*, D, D*, n, n*, o, o*, p and p* are defined as above;

E, E*, F, F*, G and G*, independently of each other, are a natural or unnatural α-amino acid or α-imino acid;

$R^1$ and $R^{1*}$, independently of each other, a1*) are hydrogen;

carboxyl, $(C_1–C_{12})$-alkyl, which is optionally unsaturated once and which is optionally substituted by up to 2 identical or different radicals from the group hydroxyl, $(C_1–C_4)$-alkoxy, carbamoyl, $(C_1–C_8)$-alkanoyloxy, carboxyl, $(C_1–C_4)$-alkoxycarbonyl,

F, amino, $(C_1–C_7)$-alkylamino, di-$(C_1–C_7)$-alkoxycarbonylamino, benzyloxycarbonyl, benzyloxycarbonylamino, 9-fluorenylmethoxycarbonylamino, $(C_1–C_4)$-alkylsulfonyl, a radical $CONR^{12}R^{13}$ or $CONR^{12*}R^{13*}$, by up to three phenyl, by up to six hydroxyl, or by up to four $(C_1–C_8)$-alkanoyloxy;

monocyclic or bicyclic $(C_3–C_{12})$-cycloalkyl, $(C_3–C_{12})$-cycloalkyl-$(C_1–C_6)$-alkyl where the cycloalkyl moiety is in each case optionally substituted by one or two identical or different radicals from the group

F, carboxyl, hydroxyl, $(C_1–C_7)$-alkoxy, $(C_1–C_4)$-alkyl, $(C_1–C_4)$-alkyloxycarbonyl, amino, $(C_1–C_6)$-alkoxycarbonylamino, benzyloxycarbonylamino, $(C_1–C_4)$-alkylamino, and di-$(C_1–C_4)$-alkylamino;

$(C_6–C_{10})$-aryloxy-$(C_1–C_6)$alkyl, $(C_6–C_{10})$-aryl, $(C_6–C_{10})$-aryl-$(C_1–C_6)$-alkyl, in which the aryl moiety is in each case optionally substituted by one, two or three identical or different radicals from the group F, Cl, Br, hydroxyl, hydroxy-$(C_1–C_4)$-alkyl, carboxamido, mono- or di-$(C_1–C_4)$-alkylaminocarbonyl, $(C_1–C_4)$-alkoxy, $(C_1–C_4)$-alkyl, $(C_1–C_4)$-alkoxycarbonyl, amino, $(C_1–C_4)$-alkylamino, di-$(C_1–C_4)$-alkylamino, carboxyl, carbamoyl, $(C_1–C_4)$-alkoxycarbonylamino;

Het,

Het-$(C_1–C_6)$-alkyl,

Het-$(C_5–C_6)$-cycloalkyl,

Het-thio-$(C_1–C_4)$-alkyl,

Het-thio-$(C_5–C_6)$-cycloalkyl, where Het is in each case the radical of a 5- to 6-membered monocyclic or 8- to 10-membered bicyclic ring system which can be aromatic, partially hydrogenated or completely hydrogenated, which can contain, as heteroelements, one, two, three or four different radicals from the group N, O, S, NO, SO and $SO_2$, which can be substituted by 1 to 4 hydroxyl, and which is optionally monosubstituted or disubstituted as defined for $(C_6–C_{10})$-aryl under a1) and/or by oxo, or is a radical $NR^{12}R^{13}$ or $NR^{12*}R^{13*}$, respectively, or a2*)

are a radical of the formula VIII or VIII*, respectively, $$R1a—W \qquad (VIII)$$

$$R1a*—W* \qquad (VIII*)$$

in which R1a and R1a* are defined as are $R^1$ and $R^{1*}$, respectively, under a1*) and W or W* is —CO—, —O—CO—, —$SO_2$—, —SO—, —S—, —NHCO— or —CH(OH)—;

or in which $R^1$ and $R^{1*}$, independently of each other form, together with R11 or R11*, respectively, and the atoms carrying the latter, monocyclic, saturated or partially unsaturated, ring systems having 5–8 ring members which, in addition to carbon, can also contain 1 sulfur atom which can optionally be oxidized to the sulfoxide or sulfone;

a3*)

are a glycosyl radical which is defined as above;

$R^2$ and $R^{2*}$, independently of each other, b1*) are hydrogen, carboxyl, $(C_1–C_{10})$-alkyl which is optionally unsaturated once or twice and which is optionally substituted by up to 3 identical or different radicals from the group hydroxyl, $(C_1–C_7)$-alkoxy, $(C_1–C_7)$-alkylthio, $(C_1–C_7)$-alkylsulfinyl, $(C_1–C_7)$-alkylsulfonyl, $(C_1–C_7)$-alkanoyloxy, carboxyl, $(C_1–C_7)$-alkoxycarbonyl, Cl, Br, amino,
amidino,
guanidino,
N,N'-di-(benzyloxycarbonyl)-guanidino,
carbamoyl,
$(C_7-C_{15})$-aralkoxycarbonyl,
$(C_1-C_5)$-alkoxycarbonylamino,
$(C_7-C_{15})$-aralkoxycarbonylamino, or
9-fluorenylmethoxycarbonylamino;
$(C_3-C_{12})$-cycloalkyl,
$(C_3-C_{12})$-cycloalkyl-$(C_1-C_3)$-alkyl,
$(C_6-C_{14})$-aryl,
$(C_6-C_{14})$-aryl-$(C_1-C_3)$-alkyl, where the aryl moiety is in each case optionally substituted by one, two or three identical or different radicals from the group
F, Cl, Br, I,
hydroxyl,
$(C_1-C_7)$-alkoxy,
$(C_1-C_7)$-alkyl,
$(C_1-C_7)$-alkoxycarbonyl,
amino and
trifluoromethyl; or
Het-$(C_1-C_6)$-alkyl, where Het is the radical of a 5- or 6-membered monocyclic or 9- to 10-membered bicyclic, optionally partially or completely hydrogenated, heteroaromatic compound, having at least 1 C atom, 1–4 N atoms and/or 1–2 S atoms and/or 1–2 O atoms as ring members, which is optionally monosubstituted or disubstituted as described for the aryl moiety under a1); or b2*) form, together with $R^4$ or $R^{4*}$, respectively, and the atoms carrying the latter, pyrrolidine or piperidine which can in each case also be fused with cyclopentyl, cyclohexyl or phenyl,
or form, together with $R^3$ or $R^{3*}$, respectively, and the atoms carrying the latter, cyclic, saturated or partially unsaturated, ring systems having 3–8 ring members;

$R^3$ and $R^{3*}$, independently of each other, are
hydrogen,
methyl or
ethyl;

$R^4$ and $R^{4*}$, independently of each other, are
hydrogen,
$(C_1-C_4)$-alkyl;

$R^5$ is
hydrogen,
$(C_1-C_6)$-alkyl,
$(C_2-C_6)$-alkenyl or alkynyl,
$(C_7-C_{20})$-arylalkyl, $(C_6-C_{10})$-aryl,
an equivalent of a pharmaceutically tolerated cation or is glyceryl ester,
1,2-difatty acid glyceryl triester, O-acyloxyalkylester or 1-methyl-2-nitroethyl ester, $R^6$ is
oxygen or sulfur;

$R^7$ is defined as described under A1), $R^8$ and $R^{8*}$, independently of each other, are
hydrogen,
$(C_1-C_8)$-alkyl or form, together with $R^9$ or $R^{9*}$, respectively, and the atoms carrying the latter, pyrrolidine or piperidine which can in each case be additionally fuzed with cyclopentyl, cyclohexyl or phenyl;

$R^9$ and $R^{9*}$,
independently of each other, are defined as are $R^2$ and $R^{2*}$, respectively, under b1), or are
$(C_1-C_8)$-alkanoyloxy, or form, together with $R^{10}$ or $R^{10*}$, respectively, and the atoms carrying the latter, cyclic, saturated or partially unsaturated, ring systems having from 5 to 12 ring members; or
form, together with $R^{11}$ or $R^{11*}$, respectively, and the atoms carrying the latter, a monocyclic or bicyclic, saturated or partially unsaturated, ring system having 5–12 ring members which, in addition to carbon, can also contain 1 sulfur atom which can optionally be oxidized to the sulfoxide or sulfone;

$R^{10}$ and $R^{10*}$, independently of each other, are
hydrogen or
$(C_1-C_4)$-alkyl;

$R^{11}$ and $R^{11*}$, independently of each other, are
hydrogen,
hydroxyl,
$(C_1-C_4)$-alkanoyloxy or
$(C_1-C_4)$-alkyl;

$R^{12}$, $R^{12*}$, $R^{13}$ and $R^{13*}$, independently of each other, are
hydrogen,
$(C_1-C_8)$-alkyl which can be substituted by
amino,
$(C_1-C_4)$-alkylamino,
di-$(C_1-C_4)$-alkylamino,
carboxyl,
hydroxyl or
$(C_1-C_4)$-alkoxy,
$(C_1-C_4)$-alkoxycarbonyl,
$(C_6-C_{10})$-aryl which can be substituted as described for $R^1$ or $R^{1*}$, respectively
$(C_6-C_{10})$-aryl-$(C_1-C_4)$-alkoxycarbonyl,
Het or
Het-$(C_1-C_4)$-alkyl, where Het is defined as described for $R^1$ or $R^{1*}$, respectively, where,
in the above compounds of the formula I, one or more amide groups (—CONH—) of the main chain can be replaced by a group comprising —CH$_2$NR$^{14}$—, —CH$_2$O—, —OCH$_2$—, —CH$_2$CH$_2$—, —COCH$_2$—, —CH(OH)CH$_2$— or —COO—, or else by an amide group having reversed polarity (—NHCO—);

$R^{14}$ is
hydrogen or
$(C_1-C_4)$-alkyl;
and the physiologically tolerated salts thereof.

Compounds of the formula I are particularly preferred in which,
c1.4)
Q is a radical of the formulae IIa or IIb;
Y, A, A*, D, D*, n, n*, o and o* are defined as above,
p and p are 1;
$R^1$ and $R^{1*}$, independently of each other, are
hydrogen,
carboxyl,
$(C_1-C_{10})$-alkyl,
$(C_3-C_8)$-cycloalkyl,
$(C_3-C_8)$-cycloalkyl-$(C_1-C_{10})$-alkyl,
phenyl-$(C_1-C_8)$-alkyl which can be substituted in the phenyl moiety as described for aryl under a1*), triphenyl-($C_1$–$C_4$)-alkyl, optionally protected mono- or di-amino-($C_1$–$C_{10}$)-alkyl or amino-($C_6$–$C_{10}$)-aryl-($C_1$–$C_4$)-alkyl or amino-($C_3$–$C_{10}$)-cycloalkyl-($C_1$–$C_4$)-alkyl, such as 2-amino-3-phenylpropyl, mono-, di-, tri-, tetra-, penta- or hexa-hydroxy-($C_1$–$C_{10}$)-alkyl or -alkanoyl, ($C_1$–$C_4$)-alkoxy-($C_1$–$C_{10}$)-alkyl, ($C_1$–$C_4$)-alkoxycarbonyl-($C_1$–$C_{10}$)-alkyl, ($C_1$–$C_8$)-alkylsulfonyl, ($C_1$–$C_8$)-alkylsulfinyl, mono-, di- or tri-hydroxy-($C_1$–$C_8$)-alkylsulfonyl, mono-, di- or tri-hydroxy-($C_1$–$C_8$)-alkylsulfinyl, mono-, di-, tri- or tetra-($C_1$–$C_8$)-alkanoyloxy-($C_1$–$C_{10}$)-alkyl, ($C_1$–$C_{11}$)-alkanoyl, optionally protected amino-($C_1$–$C_{11}$)-alkanoyl, di-($C_1$–$C_7$)-alkylamino ($C_2$–$C_{11}$)-alkanoyl, ($C_1$–$C_9$)-cycloalkylcarbonyl, amino-substituted ($C_3$–$C_9$)-cycloalkylcarbonyl, amino-substituted ($C_3$–$C_9$)-cycloalkylsulfonyl, ($C_6$–$C_{10}$)-aryloxy-($C_2$–$C_7$)-alkanoyl, ($C_6$–$C_{10}$)-aryl-($C_2$–$C_7$)-alkanoyl, benzoyl, benzenesulfonyl or ($C_6$–$C_{10}$)-aryl-($C_1$–$C_4$)-alkylcarbonyl or -sulfonyl which is optionally substituted by amino, halogen, ($C_1$–$C_7$)-alkyl, ($C_1$–$C_7$)-alkoxy or ($C_1$–$C_7$)-alkoxycarbonyl, ($C_1$–$C_{10}$)-alkoxycarbonyl, substituted ($C_1$–$C_{10}$)-alkoxycarbonyl, such as 2-(trimethylsilyl)ethoxycarbonyl, 2,2,2-trichloroethoxycarbonyl or 1,1-dimethyl-2,2,2-trichloroethoxycarbonyl, ($C_6$–$C_{14}$)-aryl-($C_1$–$C_6$)-alkoxycarbonyl, ($C_6$–$C_{10}$)-aryl-($C_1$–$C_8$)-alkyl, ($C_3$–$C_{10}$)-cycloalkyl-($C_1$–$C_8$)-alkyl or ($C_1$–$C_{10}$)-alkyl which are substituted by optionally protected amino or hydroxyl, such as 2-amino-1-hydroxy-4-methylpentyl, 9-fluorenylmethoxycarbonyl, ketohexosyl, ketopentosyl, deoxyhexoketosyl, deoxypentoketosyl, aldohexosyl, aldopentosyl, deoxyhexoaldosyl, deoxypentoaldosyl, 2-amino-2-deoxyhexosyl, 2-acetamido-2-deoxyhexosyl, lactosyl or maltosyl where the linked sugars can be present in the pyranose or furanose form, Het-($C_1$–$C_6$)-alkyl, Het-carbonyl or -sulfonyl, Het-($C_1$–$C_6$)-alkylcarbonyl or -sulfonyl, Het-mercapto-($C_1$–$C_6$)alkylcarbonyl or -sulfonyl, where Het is in each case furyl, thienyl, benzothienyl, benzodioxolanyl, pyrrolyl, imidazolyl, isoxazolyl, thiazolyl, pyrazolyl, triazolyl, pyridyl, pyrimidyl, pyrazinyl, pyridazinyl, triazinyl, pyrrolidyl, piperidyl, piperazinyl, morpholino, thiomorpholino, tetrahydrofuryl, tetrahydropyryl, tetrahydrothienyl, indolyl, quinolyl or isoquinolyl, where these radicals can also be substituted by one or two identical or different radicals from the group ($C_1$–$C_4$)-alkyl, ($C_1$–$C_4$)-alkoxy, ($C_1$–$C_4$)-alkoxycarbonyl, ($C_1$–$C_4$)-alkoxycarbonylamino, hydroxyl, amino, mono- or di-($C_1$–$C_4$)-alkylamino and oxido;

$R^2$ and $R^{2*}$, independently of each other, are hydrogen, carboxyl, ($C_1$–$C_8$)-alkyl which is optionally substituted by up to 2 identical or different radicals from the group hydroxyl, ($C_1$–$C_4$)-alkoxy, ($C_1$–$C_4$)-alkylthio, ($C_1$–$C_4$)-alkylsulfinyl, ($C_1$–$C_4$)-alkylsulfonyl, ($C_1$–$C_4$)-alkanoyloxy, carboxyl, ($C_1$–$C_4$)-alkoxycarbonyl, amino, amidino, guanidino, N,N'-di-(benzyloxycarbonyl)-guanidino, carbamoyl, ($C_6$–$C_{10}$)-aryl-($C_1$–$C_3$)-alkoxycarbonyl, ($C_1$–$C_5$)-alkoxycarbonylamino, ($C_6$–$C_{10}$)-aryl-($C_1$–$C_3$)-alkoxycarbonylamino, or ($C_3$–$C_{10}$)-cycloalkyl, ($C_3$–$C_{10}$)-cycloalkyl-($C_1$–$C_3$)-alkyl, ($C_1$–$C_4$)-alkyl-($C_3$–$C_{10}$)-cycloalkyl-($C_1$–$C_3$)-alkyl, ($C_6$–$C_{10}$)-aryl, ($C_6$–$C_{10}$)-aryl-($C_1$–$C_3$)-alkyl where the aryl moiety is in each case optionally substituted by one, two or three identical or different radicals from the group F, Cl, Br, hydroxyl, ($C_1$–$C_4$)-alkoxy, ($C_1$–$C_4$)-alkyl, ($C_1$–$C_4$)-alkoxycarbonyl and amino, or Het-($C_1$–$C_4$)-alkyl where Het is defined as in the case of $R^1$ or $R^{1*}$, respectively;

$R^3$ and $R^{3*}$, independently of each other, are hydrogen or methyl;

$R^4$ and $R^{4*}$, independently of each other, are hydrogen or methyl;

$R^5$, $R^6$ and $R^7$ are defined as described above under cl.3);

$R^8$ and $R^{8*}$, independently of each other, are hydrogen, methyl, ethyl or n-propyl, or form, together with $R^9$ or $R^{9*}$, respectively, and the atoms carrying the latter, a 1,2,3,4-tetrahydroisoquinoline or a 2-azabicyclooctane skeleton;

$R^9$ and $R^{9*}$, independently of each other, are defined as are $R^2$ or $R^{2*}$, respectively, or are ($C_1$–$C_8$)-alkanoyloxy or form, together with R10 or $R^{10*}$, respectively, and the atoms carrying the latter, cyclic ring systems having from 5 to 7 ring members;

or form, together with $R^{11}$ or $R^{11*}$, a thiochromane system whose sulfur atom can optionally be oxidized to the sulfone;

$R^{10}$ and $R^{10*}$, independently of each other, are
  hydrogen or
  methyl;
$R^{11}$ and $R^{11*}$ are defined as under cl.3);
where,
in the above compounds of the formula 1, one or more amide groups (—CONH—) of the main chain can be replaced as defined above under A3);
$R^{14}$ is
  hydrogen or
  methyl;
and the physiologically tolerated salts thereof.
Compounds of the formula I are furthermore particularly preferred
in which cl.5),
Q is a radical of the formula IIa;
$R^1$ and $R^{1*}$, independently of each other, are
  hydrogen,
  carboxyl,
  $(C_1-C_8)$-alkylsulfonyl, such as
    methylsulfonyl,
    tert-butylsulfonyl or
    isopropylsulfonyl,
  $(C_1-C_8)$-alkylsulfinyl,
  $(C_1-C_8)$-mono-, di- or tri-hydroxyalkylsulfonyl, such as
    2-hydroxyethylsulfonyl or
    2-hydroxypropylsulfonyl,
  hydroxy-$(C_1-C_{10})$-alkanoyl, such as
    2-hydroxypropionyl,
    3-hydroxypropionyl,
    3-hydroxybutyryl or
    2-hydroxy-3-methylbutyryl,
  mono-, di-, tri- or tetra-hydroxy-$(C_1-C_4)$-alkyl, such as
    1,2,3-trihydroxypropyl,
    1,2-dihydroxyethyl or
    hydroxymethyl,
  $(C_1-C_8)$-alkanoyloxy-$(C_1-C_{10})$-alkyl, such as
    acetoxymethyl,
    1,2-diacetoxyethyl,
    1,2,3-triacetoxypropyl,
  $(C_1-C_{11})$-alkanoyl, such as
    n-decanoyl,
    formyl,
    acetyl,
    propionyl,
    pivaloyl,
    isovaleryl or
    isobutyryl,
  amino-$(C_1-C_{11})$-alkanoyl, such as
    3-amino-3,3-dimethylpropionyl,
    5,4-aminobutyryl,
    5-aminopentanoyl,
    6-aminohexanoyl,
  N-$(C_1-C_4)$-alkoxycarbonylamino-$(C_1-C_8)$-alkyl, such as
    4-N-tert-butoxycarbonylaminobutyryl,
    5-N-tert-butoxycarbonylaminopentanoyl,
    6-N-tert-butoxycarbonylaminohexanoyl,
  di-$(C_1-C_7)$-alkylamino-$(C_2-C_{11})$-alkanoyl, such as
    dimethylaminoacetyl,
  $(C_3-C_9)$-cycloalkylcarbonyl, such as
    cyclopropylcarbonyl,
    cyclobutylcarbonyl,
    cyclopentylcarbonyl or
    cyclohexylcarbonyl,
  amino-$(C_3-C_8)$-cycloalkylcarbonyl, such as
    2-aminocyclopropylcarbonyl,
    3-aminocyclobutylcarbonyl,
    3-aminocyclopentylcarbonyl,
    4-aminocyclohexylcarbonyl,
  amino-$(C_3-C_8)$-cycloalkylsulfonyl, such as
    3-aminocyclopentylsulfonyl,
    4-aminocyclohexylsulfonyl,
  phenyl
  triphenyl-$(C_1-C_2)$-alkyl, such as
    triphenylmethyl,
    2-triphenylethyl,
  $(C_6-C_{10})$-aryl-$(C_1-C_4)$-alkyl, such as
    benzyl,
    2-phenylethyl or
    1-naphthylmethyl,
  $(C_6-C_{10})$-aryl-$(C_2-C_7)$-alkanoyl, such as
    phenylacetyl,
    phenylpropanoyl or
    phenylbutanoyl,
  $(C_6-C_{10})$-aryloxy-$(C_2-C_7)$-alkanoyl, such as
    1-naphthyloxyacetyl or
    phenyloxyacetyl,
  benzoyl or -benzenesulfonyl which are optionally substituted by halogen, amino, $(C_1-C_7)$-alkyl, $(C_1-C_7)$-alkoxy or $(C_1-C_7)$-alkoxycarbonyl, such as
    4-chlorobenzoyl,
    4-methylbenzoyl,
    2-methoxycarbonylbenzoyl,
    4-methoxybenzoyl,
    benzenesulfonyl,
    4-methylphenylsulfonyl,
  benzylsulfonyl, benzylsulfinyl or benzylthio which are optionally substituted by halogen, amino, $(C_1-C_7)$-alkyl, $(C_1-C_7)$-alkoxy or $(C_1-C_7)$-alkoxycarbonyl, such as
    4-chlorobenzylsulfonyl,
    benzylsulfinyl,
    4-chlorobenzylthio,
  amino,
  $(C_1-C_4)$-alkoxycarbonylamino,
  $(C_1-C_{12})$-alkanoyl which is substituted by hydroxyl or amino and optionally by phenyl or cyclohexyl, such as
    2-amino-1-hydroxy-4-methylpentyl,
  $(C_6-C_{10})$-aryl- or $(C_3-C_{10})$-cycloalkyl-$(C_1-C_4)$-alkyl or $(C_1-C_8)$-alkyl which are substituted by optionally protected amino, such as
    2-amino-3-phenylpropyl or
    N-tert-butoxycarbonyl-2-amino-3-phenylpropyl,
  $(C_1-C_{10})$-alkoxycarbonyl, such as
    methoxycarbonyl,
    ethoxycarbonyl,
    isobutoxycarbonyl or
    tert-butoxycarbonyl,
  substituted $(C_1-C_{10})$-alkoxycarbonyl, such as
    2-(trimethylsilyl)ethoxycarbonyl,
    2,2,2-trichloroethoxycarbonyl,
    1,1-dimethyl-2,2,2-trichloroethoxycarbonyl,
  $(C_6-C_{14})$-aryl-$(C_1-C_6)$-alkoxycarbonyl, such as
    benzyloxycarbonyl,
    1- or 2-naphthylmethoxycarbonyl or
    9-fluorenylmethoxycarbonyl,
  1-deoxyhexoketosyl or 1-deoxypentoketosyl, such as
    1-deoxyfructos-1-yl, 1-deoxysorbos-1-yl or 1-deoxyribulos-1-yl
hexosyl or pentosyl, such as
  mannosyl, glucosyl or galactosyl,
  xylosyl, ribosyl or arabinosyl,
6-deoxyhexosyl, such as
  rhamnosyl, fucosyl or deoxyglucosyl,
aminosugar residues, such as
  2-amino-2-deoxyglucosyl,
  2-acetamido-2-deoxyglucosyl,
  2-amino-2-deoxygalactosyl or
  2-acetamido-2-deoxygalactosyl,
lactosyl,
maltosyl,
where the linked sugars can be present in the pyranose or the furanose form,
Het, such as
  2-pyridyl,
  4-pyridyl or -4-(N-oxidopyridyl),
Het-carbonyl or Het-sulfonyl, such as
  piperidino-4-carbonyl,
  morpholino-4-carbonyl,
  pyrrolyl-2-carbonyl,
  pyridyl-3-carbonyl,
  4-tert-butoxycarbonylamino-1-piperidylcarbonyl,
  4-amino-1-piperidylcarbonyl,
  4-tert-butoxycarbonylamino-1-piperidylsulfonyl,
  4-amino-1-piperidylsulfonyl,
Het-$(C_1-C_6)$-alkyl, such as
  2-pyridyl-$(C_1-C_6)$-alkyl,
  3-pyridyl-$(C_1-C_6)$-alkyl,
  4-pyridyl-$(C_1-C_6)$-alkyl,
Het-$(C_1-C_6)$-alkanoyl or Het-$(C_1-C_6)$-alkylsulfonyl, such as
  2-pyridyl-$(C_1-C_6)$-alkanoyl,
  3-pyridyl-$(C_1-C_6)$-alkanoyl,
  4-pyridyl-$(C_1-C_6)$-alkanoyl,
  2-pyridyl-$(C_1-C_6)$-alkylsulfonyl,
Het-mercapto-$(C_1-C_3)$-alkylcarbonyl, such as
  2-pyridylthioacetyl,
where Het is in each case
  pyrrolyl,
  imidazolyl,
  pyridyl,
  pyrimidyl,
  pyrrolidyl,
  piperidyl,
  quinolyl,
  isoquinolyl or
  morpholino,
    where the latter can also be substituted by one or two identical or different radicals from the group $(C_1-C_4)$-alkyl, $(C_1-C_4)$-alkoxycarbonyl, $(C_1-C_4)$-alkoxycarbonylamino, hydroxyl, amino or mono- or di-$(C_1-C_4)$-alkylamino;
$R^2$ and $R^{2*}$, independently of each other, are
  hydrogen,
  carboxyl,
  methyl, ethyl, isopropyl, n-propyl, n-butyl, isobutyl, sec-butyl, pentyl or hexyl,
  cyclohexyl,
  cyclopentylmethyl, cyclohexylmethyl or cycloheptylmethyl,
  4-methylcyclohexylmethyl,
  1-decahydronaphthylmethyl or
  2-decahydronaphthylmethyl,
  phenyl,
  benzyl,
  2-phenylethyl,
  1-naphthylmethyl or 2-naphthylmethyl,
  2-methylbenzyl, 3-methylbenzyl or 4-methylbenzyl,
  2,4,6-trimethylbenzyl,
  4-tert-butylbenzyl,
  4-tert-butoxybenzyl,
  4-hydroxybenzyl,
  4-methoxybenzyl,
  2,4-dimethoxybenzyl,
  3,4-dihydroxybenzyl,
  3,4-dimethoxybenzyl,
  (benzodioxolan-4-yl)methyl,
  4-chlorobenzyl,
  hydroxymethyl,
  1-hydroxyethyl,
  2-pyridylmethyl, 3-pyridylmethyl, 4-pyridylmethyl or 2-(4-pyridyl)ethyl,
  2-thienylmethyl or 3-thienylmethyl,
  2-(2-thienyl)ethyl or 2-(3-thienyl)ethyl,
  indol-2-ylmethyl or indol-3-ylmethyl,
  (1-methylimidazol-4-yl)methyl,
  imidazol-4-ylmethyl or imidazol-1-ylmethyl,
  2-thiazolylmethyl,
  3-pyrazolylmethyl,
  4-pyrimidylmethyl,
  2-benzo[b]thienylmethyl or 3-benzo[b]thienylmethyl,
  2-furylmethyl,
  2-(methylthio)ethyl,
  2-(methylsulfinyl)ethyl,
  2-(methylsulfonyl)ethyl,
$R^3$, $R^{3*}$, $R^4$, $R^{4*}$, $R^{10}$ and $R^{10*}$ are
  hydrogen;
$R^5$ is
  hydrogen,
  $(C_1-C_6)$-alkyl or
  an equivalent of a pharmaceutically tolerated cation;
$R^6$ is
  oxygen;
$R^8$ and $R^{8*}$, independently of each other, are
  hydrogen or
  form, together with $R^9$ or $R^{9*}$, respectively, and the atoms carrying the latter, a 1,2,3,4-tetrahydroisoquinoline or 2-azabicyclooctane skeleton;
$R^9$ and $R^{9*}$, independently of each other, are defined as are $R^2$ or $R^{2*}$, respectively, or are
  hydroxyl,
  acetoxy,
  tert-butoxymethyl,
  3-guanidinopropyl,
  carbamoylmethyl or carbamoylethyl,
  carboxymethyl or carboxyethyl,
  mercaptomethyl,
  (1-mercapto-1-methyl)ethyl,
  aminomethyl, 2-aminoethyl, 3-aminopropyl or 4-aminobutyl,
  N,N-dimethylamino, N,N'-di(benzyloxycarbonyl)guanidinopropyl,
2-benzyloxycarbonylethyl, benzyloxycarbonylmethyl or tert-butylsulfonylmethyl or
4-benzylcarbonylaminobutyl;

$R^{11}$ and $R^{11}*$, independently of each other, are
hydrogen,
hydroxyl or
acetoxy;

where,
in the above compounds of this invention, one or more amide groups (—CONH—) of the main chain can be replaced by —$CH_2NR^{14}$— or —$CH(OH)CH_2$—;

$R^{14}$ is
hydrogen or
methyl;

and the physiologically tolerated salts thereof.

Compounds of the formula I are very particularly preferred, cl.6), in which Q is a radical of the formula IIa;

$R^1$ and $R^1*$, independently of each other, are
hydrogen,
carboxyl,
($C_1$–$C_8$)-alkylsulfonyl, such as
methylsulfonyl,
tert-butylsulfonyl or
isopropylsulfonyl,
($C_1$–$C_8$)-mono- or di-hydroxyalkylsulfonyl, such as
2-hydroxyethylsulfonyl or
2-hydroxypropylsulfonyl,
mono-, di- or tri-hydroxy-($C_1$–$C_3$)-alkyl, such as
1,2,3-trihydroxypropyl,
1,2-dihydroxyethyl or
hydroxymethyl,
($C_1$–$C_8$)-alkanoyl, such as
butanoyl,
($C_6$–$C_{10}$)-aryloxy-($C_1$–$C_4$)-alkanoyl, such as
1- or 2-naphthyloxyacetyl,
($C_6$–$C_{10}$)-aryl-($C_1$–$C_4$)-alkanoyl, such as
1- or 2-naphthylacetyl,
($C_1$–$C_8$)-alkoxycarbonyl, such as
methoxycarbonyl,
ethoxycarbonyl,
isobutoxycarbonyl or
tert-butoxycarbonyl,
($C_6$–$C_{10}$)-aryl-($C_1$–$C_4$)-alkoxycarbonyl, such as
benzyloxycarbonyl or
1- or 2-naphthylmethoxycarbonyl,
9-fluorenylmethoxycarbonyl,
($C_1$–$C_4$)-alkanoyloxy-($C_1$–$C_6$)-alkyl, such as
acetoxymethyl,
1,2-diacetoxyethyl,
1,2,3-triacetoxypropyl,
phenyl,
triphenylmethyl,
($C_6$–$C_{10}$)-aryl-($C_1$–$C_4$)-alkyl, such as
benzyl,
benzenesulfonyl which is optionally substituted by halogen, amino, ($C_1$–$C_4$)-alkyl or methoxy, such as
benzenesulfonyl,
4-methlylphenylsulfonyl,
benzylsulfonyl, benzylsulfinyl or benzylthio which is optionally substituted by halogen, amino, ($C_1$–$C_4$)-alkyl or methoxy, such as 4-chlorobenzylsulfonyl,
benzylsulfinyl or
4-chlorobenzylthio,
Het, such as 2- or 4-pyridyl or
4-(N-oxidopyridyl),
Het-carbonyl or Het-sulfonyl, such as
4-tert-butoxycarbonylamino-1-piperidylcarbonyl,
4-amino-1-piperidylcarbonyl,
2-quinolylcarbonyl,
4-tert-butoxycarbonylamino-1-piperidylsulfonyl,
4-amino-1-piperidylsulfonyl,
Het-($C_1$–$C_4$)-alkylsulfonyl, such as
2-(4-pyridyl)-ethylsulfonyl,
Het-($C_1$–$C_4$)-alkanoyl, such as
2-pyridylacetyl or
3-pyridylacetyl,
Het-mercapto-($C_1$–$C_3$)-alkylcarbonyl, such as
2-pyridylthioacetyl,
where Het is in each case
pyrrolyl,
imidazolyl,
pyridyl,
pyrimidyl,
pyrrolidyl,
piperidyl,
quinolyl,
isoquinolyl or
morpholino,
where this radical can also be substituted by one or two identical or different radicals from the group methyl, amino and ($C_1$–$C_4$)-alkoxycarbonylamino,
amino-($C_3$–$C_6$)-cycloalkylcarbonyl, such as
2-aminocyclopropylcarbonyl,
3-aminocyclobutylcarbonyl,
3-aminocyclopentylcarbonyl,
4-aminocyclohexylcarbonyl,
($C_1$–$C_8$)-alkanoyl which is substituted by hydroxyl and amino and optionally by phenyl or cyclohexyl, such as
2-amino-1-hydroxy-4-methylpentyl,
phenyl- or cyclohexyl-($C_1$–$C_6$)-alkyl which is substituted by optionally protected amino, such as
2-amino-3-phenylpropyl or
N-tert-butoxycarbonyl-2-amino-3-phenylpropyl,
amino,
($C_1$–$C_4$)-alkoxycarbonylamino,
benzyloxycarbonylamino,
1-deoxyhexoketosyl or 1-deoxypentoketosyl, such as
1-deoxyfructos-1-yl, 1-deoxysorbos-1-yl or
1-deoxyribulos-1-yl,
hexosyl or pentosyl, such as
mannosyl, glucosyl or galactosyl, or
xylosyl, ribosyl or arabinosyl, where the linked sugars can be present in the pyranose or the furanose form, $R^2$ and $R^2*$, independently of each other, are
hydrogen, methyl, ethyl, isopropyl, n-propyl, n-butyl, isobutyl, sec-butyl, pentyl or hexyl,
cyclopentylmethyl or cyclohexylmethyl,
4-methylcyclohexylmethyl,
phenyl,
benzyl,
2-phenylethyl,
1-naphthylmethyl or 2-naphthylmethyl,
2-methylbenzyl, 3-methylbenzyl or 4-methylbenzyl, 2,4,6-trimethylbenzyl,
4-tert-butylbenzyl,
4-methoxybenzyl,
3,4-dihydroxybenzyl,
3,4-dimethoxybenzyl,
2-pyridylmethyl, 3-pyridylmethyl, 4-pyridylmethyl, or 2-(4-pyridyl)ethyl,
$R^3$, $R^{3*}$, $R^4$, $R^{4*}$, $R^{10}$ and $R^{10*}$ are hydrogen;
$R^5$ and $R^6$ are defined as described under c1.5);
$R^8$ and $R^{8*}$, independently of each other, are
  hydrogen or
  form, together with $R^9$ or $R^{9*}$, respectively, and the atoms carrying the latter, a 1,2,3,4-tetrahydroisoquinoline or 2-azabicyclooctane skeleton;
$R^9$ and $R^{9*}$,
  independently of each other, are defined as are $R^9$ and $R^{9*}$, respectively, under c1.5);
$R^{11}$ and $R^{11*}$, independently of each other, are
  hydrogen,
  hydroxyl or
  acetoxy;
where,
in the above compounds of this invention, one or more amide groups (—CONH—) of the main chain can be replaced by —CH$_2$NH— or —CH(OH)CH$_2$—;
and the physiologically tolerated salts thereof.

Compounds of the formula I are furthermore paticularly preferred in which c1.7),
the radicals and symbols with and without an asterisk are in each case identical,
Q is a radical of the formula IIa,
Y is oxygen,
A is a radical of the formula IV in which
  E, F or G are Gly, Ala, Val, Leu, Ile, Nva, Nle, Phe, Tyr, Asp or Glu, and
  n+o+p is 0 or 1,
D is $R^1$ or a radical of the formulae V or VI,
$R^1$ is hydrogen, (C$_1$–C$_6$)-alkylsulfonyl, (C$_6$–C$_{10}$)-aryl-(C$_1$–C$_2$)-alkyl, triphenylmethyl, (C$_1$–C$_6$)-alkoxycarbonyl, (C$_6$–C$_{10}$)-aryl-(C$_1$–C$_2$)-alkanoyl, (C$_6$–C$_{10}$)-aryloxy-(C$_{1-C2}$)-alkanoyl, Het-carbonyl or (C$_6$–C$_{10}$)-aryl-(C$_1$–C$_2$)-alkoxycarbonyl,
$R^2$ is hydrogen, phenyl, benzyl, methyl, ethyl, isopropyl, n-propyl, n-butyl, isobutyl, sec-butyl, pentyl or cyclohexylmethyl,
$R^3$, $R^4$, $R^8$, $R^{10}$ and $R^{11}$ are hydrogen,
$R^5$ is hydrogen or (C$_1$–C$_6$)-alkyl,
$R^6$ is oxygen, and
$R^9$ is hydrogen, n-propyl, isopropyl, n-butyl, sec-butyl, isobutyl, benzyl, carboxymethyl, carboxyethyl, 1-naphthylmethyl, 2-naphthylmethyl, 2-(methylthio) ethyl, 2-(methylsulfinyl)ethyl, 2-(methylsulfonyl)ethyl, indol-2-ylmethyl or indol-3-ylmethyl,
and the physiologically tolerated salts thereof.

Compounds of the formula I, c1.8), may likewise be particularly preferably mentioned in which the radicals and symbols with and without an asterisk are in each case identical,
Q is a radical of the formula IIa,
Y is oxygen;
A is a radical of the formula IV, where
  E, F or G is Val, Phe, Ile or Asp, and
  n+o+p is 0 or 1;
D is $R^1$ or a radical of the formulae V or VI;
$R^1$ is hydrogen, (C$_1$–C$_6$)-alkylsulfonyl, phenyl-(C$_1$–C$_2$)-alkyl, triphenylmethyl, (C$_1$–C$_6$)-alkoxycarbonyl or phenyl-(C$_1$–C$_2$)-alkoxycarbonyl, $R^2$ is hydrogen, phenyl, benzyl, methyl, ethyl, isopropyl, n-propyl, n-butyl, isobutyl, sec-butyl, pentyl or cyclohexylmethyl,
$R^3$, $R^4$, $R^8$, $R^{10}$ and $R^{11}$ are hydrogen,
$R^5$ is hydrogen or (C$_1$–C$_4$)-alkyl,
$R^6$ is oxygen, and
$R^9$ is hydrogen, isopropyl, sec-butyl, benzyl, carboxymethyl, 1-naphthylmethyl, 2-(methylthio)-ethyl or indol-2-ylmethyl,
and the physiologically tolerated salts thereof.

The present invention furthermore relates to a process for preparing compounds of the formula I, wherein a fragment having a terminal carboxyl group, or a reactive derivative of this fragment, is coupled to a corresponding fragment having a free amino group, (a) protective group(s) which has/have, where appropriate, been temporarily introduced to protect further functional groups is/are eliminated, and the compound thus obtained is, where appropriate, converted into its physiologically tolerated salt.

Fragments of a compound of the formula I having a terminal carboxyl group possess the following formulae, for example:

| | |
|---|---|
| D - OH | (VIII) |
| D - E - OH | (IX) |
| D - F - OH | (X) |
| D - G - OH | (XI) |
| D - E - F - OH | (XII) |
| D - E - G - OH | (XIII) |
| D - F - G - OH | (XIV) |
| D - E - F - G - OH | (XIVa) |

The same is correspondingly true for the analogous radicals marked with an asterisk.

Fragments of a compound of the formula I having a terminal amino group possess the following formulae, for example:

| | |
|---|---|
| H—Z—H | (XV) |
| H—G—Z—G*—H | (XVI) |
| H—F—Z—F*—H | (XVIa) |
| H—E—Z—E*—H | (XVIb) |
| H—F—G—Z—G*—F*—H | |
| H—E—G—Z—G*—E*—H | (XVIIa) |
| H—E—F—Z—F*—E*—H | (XVIIb) |
| H—E—F—G—Z—G*—F*—E*—H | (XVIII) | where Z is a radical of the formula (XIX):

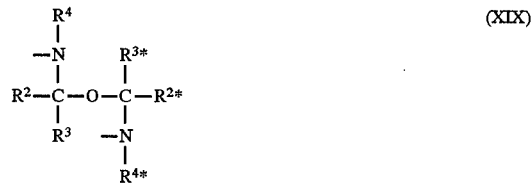

(XIX)

In the event that the two radicals bonded to Q are different, other fragments besides those of the formulae XV to XVIII, which may possibly be protected at a terminal amino group, can also be employed.

Methods which are suitable for preparing an amide bond are described, for example, in Houben-Weyl, Methoden der organischen Chemie [Methods of organic chemistry], Volume 15/2; Bodansky et al., Peptide Synthesis. 2nd ed. (Wiley & Sons, New York 1976) or Gross, Meienhofer, The Peptides: Analysis, synthesis, biology (Academic Press, New York 1979). Use is preferably made of the following methods: active ester method using N-hydroxysuccinimide, 1-hydroxybenzotriazole or 3-hydroxy-4-oxo-3,4-dihydro-1, 2,3-benzotriazine as the alcohol component, coupling with a carbodiimide such as dicyclohexylcarbodiimide (DCC) or with n-propanephosphonic anhydride (PPA) and the mixed anhydride method using pyvaloyl chloride or ethyl chloroformate or isobutyl chloroformate, or coupling with phosphonium reagents such as benzotriazol-1-yloxy-tris(dimethylamino)phosphonium hexafluorophosphate (BOP) or uronium reagents such as 2-(1H-benzotriazol-1-yl)-1,1, 3,3-tetramethyluronium tetrafluoroborate (TBTU).

Fragments of the formula (VIII) or (VIII*) are synthesized, provided they a) fall within formula (V) or (V*), in accordance with the general methods for preparing amino acids;

b) fall within formula (VI) or (VI*), proceeding, for example, from the corresponding amino acids, with the centers of chirality of these amino acids being retained. Diazotization at from $-20°$ C. to $50°$ C. in dilute mineral acids gives rise to $\alpha$-bromocarboxylic acids or, via the lactic acids, to $\alpha$-trifluoromethanesulfonyloxycarboxylic acids which can be reacted with a nucleophile carrying $R^1$ and $R^{11}$ or $R^{1*}$ and $R^{11*}$, respectively, or are prepared, for example, proceeding from malonic esters whose alkylation yields mono-substituted or di-substituted malonic esters which, following hydrolysis, are converted by means of decarboxylation into the desired derivatives;

c) fall within formula (VII) or (VII*), proceeding from the corresponding $\alpha$-amino acids, with the centers of chirality of these amino acids being retained. Diazotization at from $-20°$ C. to $50°$ C. in dilute mineral acids gives rise to lactic acids which can be reacted with an electrophile carrying a $R^1$ or $R^{1*}$.

Fragments of the formulae (IX), (X), (XI), (XII) and (XIII), (XIV) and (XIVa) are synthesized in accordance with the general, known methods for preparing amino acids and peptides.

Fragments of the formula XV are synthesized in accordance with known processes (K. Sasse in Houben-Weyl, Methoden der organischen Chemie [Methods of organic chemistry], Volume 12/1, Georg Thieme Verlag, Stuttgart, 1963; U. H. Felcht in Houben-Weyl, Methoden der organischen Chemie [Methods of organic chemistry], Volume 12/E/2, Georg Thieme Verlag, Stuttgart, 1982; D. Redmore in Griffiths, Ed., Phosphorus Chemistry, vol. 8, p. 515). Use is preferably made of the following methods:

1) Synthesis of the Compounds of the Formula XVa

B Z B                                          (XVa)

where B is protective groups, in particular benzyloxycarbonyl, by reacting substituted $\alpha$-aminophosphonites, which are prepared by known methods (J. Org. Chem. 53 (1988) 4500), e.g. ethyl 1-benzyloxycarbonylamino-2-phenylethylphosphonite, with substituted $\alpha$-aminoaldehydes, which are prepared by known methods, e.g. N-benzyloxycarbonylamino-L-phenylalaninal (Lit. Tetrahedron Lett 22 (1988) 3815; ibid 31 (1990) 7359).

The reactions are carried out in an organic solvent, preferably chloroform, by means of base catalysis, preferably using triethylamine at from $-78°$ C. to $100°$ C., preferably at approximately $60°$ C.

Peptide analogs of this nature can be prepared by known methods which can be found, for example, in the following references:

A. F. Spatola in "Chemistry and Biochemistry of Amino Acids Peptides and Proteins" 1983 (B. Weinstein et al. eds.) Marcel Dekker, New York, p. 267 (Review article);

J. S. Morley, Trends Pharm Sci. (1980), pp. 463–468 (Review article); D. Hudson et al., Int. J. Pept. Prot. Res. (1979), 14, 177–185 (—$CH_2NH$—, —$CH_2CH_2$—);

A. F. Spatola et al., Life Sci. (1986), 38, 1243–1249 (—$CH_2$—S—);

M. M. Hann, J. Chem. Soc. Perkin Trans. I (1982) 307–314 (—CH=CH— cis and trans);

J. K. Whitesell et al., Chirality 1, (1989) 89–91 (—CH=CH— trans)

R. G. Almquist et al., J. Med. Chem. (1980), 23, 1392–1398 (—$COCH_2$—);

C. Jennings-White et al., Tetrahedron Lett. (1982) 23, 2533 (—$COCH_2$—);

M. Szelke et al., EP-A 45665 (1982), CA: 97: 39405 (—$CH(OH)CH_2$—);

M. W. Holladay et al., Tetrahedron Lett. (1983) 24, 4401–4404 (—$CH(OH)CH_2$—);

V. J. Hruby, Life Sci. (1982), 31, 189–199 (—$CH_2$—S—);

N. E. Jacobsen, P. A. Barlett, J. Am. Chem. Soc. (1981) 103, 654–657 (—P(O)(OR)NH—).

The preliminary operations and final operations which have to be carried out in association with preparing compounds of the formula I, such as the introduction and elimination of protective groups, are known from the literature and are described, for example, in T. W. Greene "Protective Groups in Organic Synthesis" (John Wiley & Sons, New York, 1981). Salts of compounds of the formula I having salt-forming groups are prepared, in a manner known per se, by, for example, reacting a compound of the formula I having a basic group with a stoichiometric quantity of a suitable acid or reacting compounds of the formula I having an acid group with a stoichiometric quantity of a suitable base. Stereoisomeric mixtures, in particular diastereomeric mixtures, which may result in association with the synthesis of compounds of the formula I can be resolved, in a manner known per se, by fractional crystallization or by chromatography.

The compounds of the formula I according to the invention exhibit enzyme-inhibiting properties. In particular, they inhibit HIV protease. Their enzyme-inhibitory effect, which is in the milli- to subnano-molar range, can be determined as follows.

Test Principle

The substrates of the HIV protease which have been employed thus far include the heptapeptide: H-Ser-Phe-Asn-Phe-Pro-Gln-Ile-OH (SEQ ID NO. 1) (P. L. Darke et al., Biophys. Res. Commun. 156 (1988) 297–303). When this peptide is used as the substrate, the HIV protease cleaves it between the second Phe and the Pro.

It has now been found, surprisingly, that substituting 5-oxaproline for proline in this sequence gives rise to a substrate which can be cleaved considerably faster by the HIV protease and thus permits more rapid analysis requiring smaller quantities of enzyme.

General instructions for testing inhibitors of the HIV proteases:

a) Preparation of the Substrate Solution 2 mg of H-Ser-Phe-Asn-Phe-Opr-Gln-Ile-OH (H-Opr-OH=5-oxaproline) (SEQ ID NO. 1) are dissolved in 1 ml of MGTE 15 buffer (use of ultrasonication if required) and this solution is subsequently filtered through a sterilizing filter (0.45 μm).

b) Preparation of the Inhibitor Solution 2.5 times the necessary quantity of inhibitor to give the desired molarity per ml of solution is weighed out and dissolved in DMSO (10% of the final volume). This solution is diluted with MGTE 15 buffer to the final volume and then filtered through a sterilizing filter (0.45 μm).

c) Preparation of the Protease Solution

5 μl of the HIV protease solution are diluted with MGTE25 buffer as required.

d) Implementation of the Test

In each case, 10 μl of the substrate solution are pipetted into a test tube (16×100) having a screw cap. 10 μl of MGTE 15 buffer, which contains 10% DMSO, are pipetted in for the blank experiment. 10 μl of the inihibitor solutions are added to each of the remaining test tubes. The tubes are incubated at 37° C. for 5–10 minutes and 5 μl of the protease solution are then added to each sample. Following reaction at 37° C. for 2 hours, 10 or 20 μl (depending on the sensitivity of the HPLC equipment) are pipetted out from each sample, added to microvials and diluted with 120 μl of the HPLC eluant.

e) Conditions for the HPLC Analysis

Eluant system:

80% 0.1M phosphoric acid, pH 2.5

20% (w/w) acetonitrile

Column: Merck ®LICHROSORB RP18 (5 μm) 250×4

Rate of flow: 1 ml/min

Temperature of the column: 42° C.

Detector parameters: 215 nm, 0.08 AUF, 18.2° C.

Analysis time: 11 minutes

Retention time for the substrate: 8.1 minutes

Retention time for the N-terminal tetrapeptide: 3.9 minutes f) Solvents Required 1) MGTE 15 buffer:

20 mM morpholinoethanesulfonic acid (MES)

15% (w/v) glycerol 0.1% (v/v) Triton×100

5 mM EDTA 0.5M NaCl 1 mM phenylmethylsulfonyl fluoride (PMSF)

2) MGTE 25 buffer:

Composition similar to that of MGTE 15 buffer with the following differences:

25% (w/v) glycerol, and, in addition, 1 mM dithiothreitol (DTT)

MES, EDTA, NaCl, DTT and PMSF are weighed into a conical flask and dissolved in a little water, and this solution is adjusted to pH 6. The appropriate quantity of glycerol is weighed into a volumetric flask and ®Triton×100 is added to it by pipette. The aqueous solution is transferred into the volumetric flask, which is filled to the mark with water.

3) HPLC Eluant

A 0.1M solution of ortho-phosphoric acid (FLUKA puriss. p.a.) is prepared. This solution is adjusted precisely to pH 2.5 using triethylamine (FLUKA puriss. p.a.). The weight of the solution is determined and the appropriate quantity of acetonitrile (fume cupboard!) is weighed into it. The constituents are mixed thoroughly and degassed for about 5 minutes using helium 5.0.

g) Evaluation

Under the conditions chosen for this experiment, the heptapeptide is separated from the N-terminal tetrapeptide resulting from the enzymic cleavage. The % content of tetrapeptide peak related to the sum of tetrapeptide+heptapeptide gives the cleavage rate. The following $IC_{50}$ values indicate the inhibitor concentrations at which the cleavage rate is halved:

| Example | $IC_{50}$ |
| --- | --- |
| No. 3 | 70 nM |
| 4 | 1.3 nM |
| 7 | 15 nM |
| 8 | 0.5 nM |
| 10 | 4.2 nM |

The target peptide was assembled step-wise using a model 430 A peptide synthesizer from Applied Biosystems, and using the Fmoc method, on a p-benzyloxybenzylalcohol resin, which was esterified with Fmoc-Ile-OH, from Novabiochem (loading, approximately 0.5 mmol/h of resin). 1 g of the resin was employed and the synthesis was carried out using a synthesis program which was modified for the Fmoc method.

The following amino acid derivatives are used: Fmoc-Gln-OH, Fmoc-Opr-OH, Fmoc-Phe-OObt, Fmoc-Asn-OH and Fmoc-Ser(tBu)-OObt. In order to synthesize FmocOpr-OH, H-Opr-OtBu was synthesized by the method of Vasella et al. (J. C. S. Chem. Comm. 1981, 97–98) and, reacted with Fmoc-OSu in 15 dioxane/water (1:1) in the presence of $NaHCO_3$. Subsequent cleavage of the tert-butyl ester with trifluoroacetic acid yields Fmoc-Opr-OH.

1 mmol of the amino acid derivatives having a free carboxyl group was in each case weighed into the cartridges of the synthesizer together with 0.95 mmol of HOObt. These amino acids were pre-activated directly in the cartridges by dissolving them in 4 ml of DMF and adding 2 ml of a 0.55 molar solution of diisopropylcarbodiimide in DMF. The HOObt esters of the other amino acids were dissolved in 6 ml of NMP and then, like the in-situ pre-activated amino acids, coupled to the resin, which had previously been unblocked using 20% piperidine in DMF. Once the synthesis was complete, the peptide was cleaved off from the resin, with the side-chain protective groups being simultaneously removed, with trifluoroacetic acid using thioanisole and ethanedithiol as cation-capturing agents. The residue obtained after stripping off the trifluoroacetic acid was digested several times with ethyl acetate and centrifuged.

The remaining residue was chromatographed on an alkylated dextran gel using 10% acetic acid. The fraction containing the pure peptide was combined and freeze-dried.

Mass spectrum (FAB): 854 (M+H+) Amino acid analysis: Asp: 0.98; Ser: 0.80; Glu: 1.00; Ile: 1.05; Phe: 2.10; $NH_3$: 1.76.

The invention also relates to the use of the compounds of the formula I as medicines and pharmaceutical preparations which contain this compound. Their use in primates, in particular in humans, is preferred.

Pharmaceutical preparations contain an effective quantity of the active compound of the formula I together with an inorganic or organic pharmaceutically utilizable carrier substance. Administration can be effected intranasally, intravenously, subcutaneously or perorally. The dosage which is to be used of the active compound depends on the homeothermic species, the bodyweight, the age and the route of administration.

The pharmaceutical preparations of the present invention are produced by dissolution processes, mixing processes, granulating processes or coating processes which are known per se.

For an oral application form, the active compounds are mixed with the additives which are customary for this purpose, such as carrier substances, stabilizers or inert diluents, and brought, by customary methods, into suitable forms for administration, such as tablets, coated tablets, hard gelatine capsules, aqueous, alcoholic or oily suspensions, or aqueous, alcoholic or oily solutions. Gum arabic, magnesium oxide, magnesium carbonate, potassium phosphate, lactose, glucose, magnesium stearylfumarate or starch, in particular corn starch, can, for example, be used as inert excipients. In this context, the preparation can be effected as a dry granulate or as a wet granulate. Vegetable or animal oils, such as sunflower oil and cod-liver oil, are, for example, suitable for use as oily carrier substances or solvents.

For subcutaneous or intravenous administration, the active compounds, or their physiologically tolerated salts, are brought into solution, suspensions or emulsions, if desired together with the substances which are customary for this purpose, such as solubilizers, emulsifiers or other auxiliary substances. Examples of suitable solvents are: water, physiological solutions of sodium chloride, or alchohols, e.g. ethanol, propanediol or glycerol, and also sugar solutions, such as solutions of glucose or mannitol, or else a mixture of the different solvents which have been mentioned.

It is also possible to use injectable control-release preparations. Examples of pharmaceutical forms which can be used are oily crystal suspensions, microcapsules, rods or implants, it being possible for the latter to be made of tissue-compatible polymers, in particular biodegradable polymers, such as, for example, those based on polylactic acid/polyglycolic acid copolymers, or human albumin.

List of Abbreviations
Boc tert-butyloxycarbonyl
Chg cyclohexylglycl
d doublet
TLC thin layer chromatography
DCC dicyclohexylcarbodiimide
DCM dichloromethane
DMF dimethylformamide
DMAP 4-dimethylaminopyridine
DMSO dimethyl sulfoxide
EDAC 1-(3-dimethylaminopropyl)-3-ethylcarbodiimide hydrochloride
EA ethyl acetate
FAB fast atom bombardment
HOBt hydroxybenzotriazole
i. V. in vacuo
m multiplet
M molecular peak
NEM N-ethylmorpholine
Npg neopentylglycyl
MS mass spectrum
PPA n-propylphosphonic anhydride
RT room temperature
s singlet
m.p. melting point
t triplet
Tbg tert-butylglycyl
TBTU 2-(1H-benzotriazol-1-yl)-1,1,3,3-tetramethyluronium tetrafluoroborate
THF tetrahydrofuran
Thia 2-thienylalanyl
Z benzyloxycarbonyl The other abbreviations used for amino acids conform to the three-letter code which is customary in peptide chemistry (as described, for example, in Eur. J. Biochem. 138, (1984), 9–37). Unless expressely indicated otherwise, an amino acid is always in the L configuration.

The following examples serve to illustrate the present invention without restricting it thereto.

EXAMPLE 1 a) 1-Diphenylmethylamino-2-phenylethylphosphonous acid

A solution of 17.59 g (0.124 mol) of phenyl acetaldehyde in 20 ml of dioxane is slowly added dropwise to a suspension, which is heated at 100° C. under argon, of 31.85 g (0.124 mol) of diphenylmethylaminohypophosphite in 350 ml of dioxane, prepared by mixing equimolar quantities of diphenylmethylamine and hypophosphorous acid (100%) in ethanol. The reaction solution is stirred at this temperature for 1 h. The water of reaction which has formed is removed by azeotropic distillation using 280 ml of dioxane. Once the reaction solution has been cooled down and diluted with 150 ml of ethanol, the product, which slowly precipitates out, is filtered off with suction, washed with ethanol/diethyl ether and dried over $P_2O_5$. Yield: 9.84 g (22.5%); m.p.: 209°–211° C.; MS: 352 (M+H)$^+$; 286; 167.

b) 1-Amino-2-phenylethylphosphonous acid 9.9 g (0.028 mol) of 1-diphenylmethylamino-2-phenylethylphosphonous acid are heated, at 100°–105° C. for 2 h, in 50 ml of 40% hydrobromic acid. The reaction solution is then evaporated to dryness i.V. and the residue is taken up in 50 ml of water. The aqueous solution is washed several times with diethyl ether and evaporated to dryness. The residue is dissolved in 60 ml of ethanol and propylene oxide is added to the solution until the product precipitates out. After the mixture has been left to stand overnight, the precipitate is filtered off with suction, washed with ethanol/diethyl ether and dried.

Yield: 4.23 g (82%); m.p.: 225°–226° C.; MS: 186 (M+H)$^+$; 120 c) 1-Benzyloxycarbonylamino-2-phenylethylphosphonous acid 2.25 ml (14.25 mmol) of benzyl chloroformate are added dropwise, at 0° C. and within the space of 30 min., to a suspension of 1.76 g (9.5 mmol) of 1-amino-2-phenylethylphosponous acid in 15 ml of 1M NaOH, 5 ml of water and 5 ml of dioxane. During a further 2.5 h of stirring at 0° C., the pH of the mixture is maintained at 9–10 using 1M NaOH (approximately 10 ml). After removing the cooling medium, the mixture is stirred at RT overnight. The reaction solution is then washed several times with diethyl ether. The aqueous phase is adjusted to pH 2, at 0°–5° C., using 6M HCl and extracted several times with ethyl acetate. The combined extracts are washed with a saturated solution of NaCl, dried with $Na_2SO_4$, filtered and subjected to rotary evaporation i.V. A solid residue remains which is recrystallized from ether/petroleum ether.

Yield: 2.62 g (86%); MS: 342 (M+Na)$^+$, 320 (M+H)$^+$; 254 m.p.: 136°–137° C.

d) Ethyl 1-benzyloxycarbonylamino-2-phenylethylphosphonite 2.24 ml (25 mmol) of pyridine are added dropwise, at RT and within the space of 20 min., to a suspension of 7.98 g (25 mmol) of 1-benzyloxycarbonylamino-2-phenylethylphosphonous acid and 2.53 ml (25 mmol) of ethyl chloroformate under argon in 200 ml of chloroform. The reaction solution is stirred for a further 30 min. at this temperature. It is then heated at 70° C. for 1 h. After the solvent has been evaporated off i.V., the residue is taken up in ethyl acetate, washed with water and a saturated solution of NaCl, dried over $Na_2SO_4$, filtered and evaporated i.V. The solid residue which remains is recrystallized from ether/petroleum ether.

Yield: 7.6 g (88%); MS: 348 (M+H)$^+$; 254; 210 e) 2-Benzyloxycarbonyl-L-phenylalanine-N-methoxy-N-methylamide 31.8 ml (0.18 mol) of N-ethyldiisopropylamine are added dropwise, at 0° C., to a solution of 17.94 g (0.06 mol) of benzyloxycarbonylphenylalanine, 5.97 g (0.06 mol) of N,O-dimethylhydroxylamine hydrochloride, 8.79 g (0.06 mol) of ethyl hydroxyiminocyanoacetate and 19.68 g (0.06 mol) of TOTU in 120 ml of DMF. The mixture is stirred at 0° C. for 1 h and at RT for 3 h. The solvent is removed by rotary evaporation i.V. and the residue is taken up in ethyl acetate; the solution thus obtained is washed several times with a 10% solution of citric acid, with a 10% solution of $KHCO_3$ and with a saturated solution of NaCl. Once the solution has been dried over $Na_2SO_4$ and filtered, and the filtrate has been concentrated, 13.95 g (68%) of an oil remain.

MS: 343 $(M+H)^+$ f) N-Benzyloxycarbonyl-L-phenylalaninal 4.35 g (12.71 mmol) of 2-benzyloxycarbonyl-L-phenylalanine-N-methoxy-N-methylamide, dissolved in 40 ml of diethyl ether, are added dropwise, within the space of 30 min., to a suspension, which is stirred at 0° C. under argon, of 0.965 g (25.42 mmol) of lithium aluminum hydride in 140 ml of diethyl ether. After a further 30 min., the cooling medium is removed and the mixture is stirred at RT for 30 min. 50 ml of ice water are then added carefully to it and this mixture is filtered. The filtrate is adjusted to pH 4 using 10% $H_2SO_4$ and extracted several times with ether. The combined ether extracts are washed with water and a saturated solution of NaCl, dried over $Na_2SO_4$, filtered and freed from solvent i.V.

The oily product remains.

Yield: 3.41 g (95%); MS: 284 $(M+H)^+$; 254; 240; 210 g) Ethyl 1-(2-benzyloxycarbonylamino-1-hydroxy-3-phenylpropyl),1-(1-benzyloxycarbonylamino-2-phenylethyl)phosphinate A solution of 4.18 g (12 mmol) of ethyl 1-benzyloxycarbonylamino-2-phenylethylphosphonite, 3.41 g (12 mmol) of N-benzyloxycarbonyl-L-phenylalaninal and 0.85 ml (6 mmol) of triethylamine in 100 ml of chloroform is stirred, under argon, at RT for 20 h. A further 0.85 ml (6 mmol) of triethylamine is then added. The mixture is boiled at reflux for 9 h. Once the solvent has been removed by rotary evaporation, the residue is dissolved in 200 ml of ethyl acetate and this solution is washed several times with water and a saturated solution of NaCl. The org. phase is dried with $Na_2SO_4$, filtered and subjected to rotary evaporation i.V. The residue is purified by chromatography on silica gel (ethyl acetate/n-heptane: 5/1).

Yield: Isomer A, 1.74 g (23%); isomer B, 0.81 g (11%) MS: 631 $(M+H)^+$; 240; 210

EXAMPLE 2

Ethyl 1-(2-amino-1-hydroxy-3-phenylpropyl),1-(1-amino-2-phenylethyl)phosphinate dihydrochloride 1.5 g (2.38 mmol) of ethyl 1-(2-benzyloxycarbonylamino-1-hydroxy-3-phenylpropyl),1-(1-benzyloxycarbonylamino-2-phenylethyl)phosphinate (isomer A) are dissolved in 80 ml of methanol and hydrogenated with $H_2$ for 3 h using 0.3 g of Pd/C (10%), during which process the pH of the reaction solution is maintained at 3 using methanolic HCl. The catalyst is filtered off and the filtrate is evaporated to dryness. The remaining product is recrystallized from isopropanol/ether.

Yield: 0.9 g (87%); MS: 363 $(M+H)^+$; 244; 120

EXAMPLE 3

Ethyl 1-{2-[(benzyloxycarbonyl-L-valyl)amino]-1-hydroxy-3-phenylpropyl},1-{1-[(benzyloxycarbonyl-L-valyl)amino]}-2-phenylethyl}phosphinate

[lacuna] are [lacuna], at 0° C., to a solution of 440 mg (1 mmol) of the compound from Example 2, 306 mg (2.5 mmol) of benzyloxycarbonylvaline, 360 mg (2.5 mmol) of ethyl hydroxyiminocyanoacetate and 820 mg (2.5 mmol) of TOTU in 40 ml of DMF and [lacuna] is stirred at RT for 4 h. The solvent is removed by rotary evaporation i.V. and the residue is dissolved in 100 ml of ethyl acetate. The ethyl acetate solution is washed several times with a 10% solution of citric acid, with a 10% solution of $KHCO_3$ and with a saturated solution of NaCl, dried over $Na_2SO_4$, filtered and evaporated to dryness i.V. The solid residue is recrystallized from ethyl acetate.

Yield: 0.58 g (70%); MS: 851 $(M+Na)^+$, 829 $(M+H)^+$

EXAMPLE 4

1-{2-[(Benzyloxycarbonyl-L-valyl)amino]-1-hydroxy-3-phenylpropyl},1-{-[(benzyloxycarbonyl-L-valyl)amino]-2-phenylethyl}phosphinic acid 0.06 ml (0.447 mmol) of trimethylsilyl bromide is added dropwise at 0° C., to a solution, under argon, of 124 mg (0.149 mmol) of the compound from Example 3 in 5 ml of tetrahydrofuran. After 1 h at this temperature and 24 h at RT, 2 ml of ice water are added to the solution and this mixture is extracted with 50 ml of ethyl acetate, filtered and evaporated i.V. A viscous oily product remains. Purification is effected by chromatography on silica gel (ethyl acetate/n-heptane: 5/1).

Yield: 25.6 mg (21.5%); MS: 823 $(M+Na)^+$; 801 $(M+H)^+$

EXAMPLE 5

Ethyl 1-[2-(L-valylamino)-1-hydroxy-3-phenylpropyl],1-[L-valylamino)-2-phenylethyl] phosphinate dihydrochloride Synthesized, in analogy with Example 2, from ethyl 1-{2-[(benzyloxycarbonyl-L-valyl)amino]-1-hydroxy-3-phenylpropyl},1-{1-[(benzyloxycarbonyl-L-valyl)amino]-2-phenylethyl}phosphinate.

Yield: 0.24 g (90%); MS: 561 $(M+H)^+$; 462; 249

EXAMPLE 6

Ethyl 1-{2-[(N-tert-butyloxycarbonyl-L-naphthylalanyl-L-valyl)amino]-1-hydroxy-3-phenylpropyl},1-{1-[(N-tert-butyloxycarbonyl-L-naphthylalanyl-L-valyl)amino]-2-phenylethyl}phosphinate 340 mg (1.64 mmol) of 1,1'-carbonyldiimidazole are added, at 0° C., to a solution of 470 mg (1.5 mmol) of N-tert-butyloxycarbonyl-L-naphthylalanine and 202 mg (1.5 mmol) of 1-hydroxybenzotriazole in 15 ml of tetrahydrofuran. The mixture is stirred at 0° C. for 15 min. and at RT for 2 h. The active ester solution thus obtained is added, also at 0° C., to a mixture comprising 320 mg (0.5 mmol) of the compound from Example 5 and 0.17 ml (1 mmol) of N-ethyldiisopropylamine in 15 ml of DMF, and this is followed by a further 0.34 ml (2 mmol) of N-ethyldiisopropylamine. The reaction mixture is then stirred at 0° C. for 2 h and at RT for 4 h. The solvent is removed by rotary evaporation i.V. and the residue is purified by chromatography on silica gel ($CH_2Cl_2/CH_3OH$: 40/1).

Yield: 360 mg (62%); MS: 1178 $(M+Na)^+$, 1156 $(M+H)^+$

EXAMPLE 7

Ethyl 1-{2-[(L-naphthylalanyl-L-valyl)amino]-1-hydroxy-3-phenylpropyl},1-{1-[(L-naphthylalanyl-L-valyl)amino]-2-phenylethyl}phosphinate bistrifluoroacetate A solution of 72 mg (0.06 mmol) of the compound obtained from Example 6 in 2 ml of trifluoroacetic acid is stirred at RT for 1 h and then evaporated to dryness i.V. The product precipitated by adding ethyl acetate is filtered off with suction, washed with ether and dried over $P_2O_5$.

Yield: 56.7 mg (80%); MS: 997.5 $(M+Na)^+$, 955.5 $(M+H)^+$

EXAMPLE 8

1-{2-[(L-Naphthylalanyl-L-valyl)amino]-1-hydroxy-3-phenylpropyl},1-{1-[(L-naphthylalanyl-L-valyl)amino]-2-phenylethyl}phosphinic acid dihydrobromide 543 mg (0.47 mmol) of the compound obtained from Example 7 are treated with 0.5 ml (3.81 mmol) of trimethylsilyl bromide in analogy with the method described in Example 4. The crude product is purified by chromatography on silica gel ($CH_2Cl_2/CH_3OH$: 5/1).

Yield: 255 mg (50%); MS: 965.8 $(M+K)^+$; 927.4 $(M+H)^+$

EXAMPLE 9

Ethyl 1-{2-[((2S(tert-butylsulfonylmethyl)-3-(1-naphthyl)-propionyl)-L-valyl)amino]-1-hydroxy-3-phenylpropyl},1-{1-[((2S(tert-butyl-sulfonylmethyl)-3-(1-naphthyl)propionyl)-L-valyl)amino]-2-phenylethyl}phosphinate 321 mg (1.56 mmol) of N,N'-dicyclohexylcarbodiimide are added, at 0° C., to a solution of 521 mg (1.56 mmol) of 2S(tert-butylsulfonylmethyl)-3-(1-naphthyl)propionic acid and 254 mg (1.56 mmol) of 3-hydroxy-4-oxo-3,4-dihydro-1,2,3-benzotriazine in 3 ml of tetrahydrofuran. The mixture is stirred at 0° C. for 30 min. and at room temperature for 20 min. After filtration, the resulting active ester solution is added, at 0° C., to a mixture comprising 330 mg (0.52 mmol) of the compound from Example 5 and 0.18 ml (1.04 mmol) of N-ethyldiisopropylamine in 30 ml of DMF, and this is followed by a further 0.36 ml (2.08 mmol) of N-ethyldiisopropylamine. The reaction mixture is then stirred at 0° C. for 2 h and at room temperature for 24 h. The solvent is removed by rotary evaporation i.V. and the residue is taken up in 150 ml of ethyl acetate. The ethyl acetate solution is washed several times with a 10% solution of citric acid, with a 10% solution of $KHCO_3$ and with a saturated solution of NaCl, dried over sodium sulfate, filtered and evaporated to dryness i.V. Purification is effected by chromatography on silica gel (ethyl acetate/n-heptane: 5/1).

Yield: Isomer A, 0.21 g (34%) Isomer B, 0.15 g (24%) MS: 1215 $(M+Na)^+$; 1193 $(M+H)^+$

EXAMPLE 10

1-{2-[((2S(tert-Butylsulfonylmethyl)-3-(1-naphthyl)-propionyl)-L-valyl)amino]-1-hydroxy-3-phenylpropyl},1-{1-[((2S(tert-butylsulfonylmethyl)-3-(1-naphthyl)propionyl)-L-valyl)amino]-2-phenylethyl}phosphinic acid 180 mg of isomer A and 120 mg of isomer B from Example 9 are treated with trimethylsilyl bromide in analogy with the method described in Example 7. The crude products are purified by chromatography on silica gel ($CH_2Cl_2/CH_3OH$: 5/1).

Yield: 88 mg (50%) of isomer A 55 mg (47%) of isomer B MS: 1209 $(M+2Na—H)^+$; 1203 $(M+K)^+$; 1187 $(M+Na)^+$

---

We claim:

1. A compound of the formula I $$\begin{array}{c} R^4 \\ | \\ A-N \quad R^{3*} \\ | \quad\quad | \\ R^2-C-\!\!-\!\!-Q-C-R^{2*} \\ | \quad\quad | \\ R^3 \quad A^*-N \\ \quad\quad\quad | \\ \quad\quad\quad R^{4*} \end{array} \quad (I)$$

in which

Q is a radical of the formula IIa or IIb $$\begin{array}{c} R^6 \;\; OH \\ \| \;\;\; | \\ -P-\!\!-\!\!-C-\!\!\!\!\diagdown \\ | \quad\quad\quad H \\ Y-R^5 \end{array} \quad (IIa)$$

$$\begin{array}{c} R^6 \;\; OH \\ \| \;\;\; | \\ -P-\!\!-\!\!-C-\!\!\!\!\diagdown \;\; ; \\ | \quad\quad\quad H \\ N-R^7 \\ | \\ R^{7*} \end{array} \quad (IIb)$$

Y is oxygen or sulfur, and

A is a radical of the formula IV and A* is a radical of the formula IV*, $$D-(E)n-F(o)-(G)p- \quad (IV)$$

$$D^*-(E^*)n^*-(F^*)o^*-(G^*)p^* \quad (IV^*)$$

where

E, E*, F, F*, G and G*, independently of each other, are a natural or unnatural amino acid, azaamino acid or imino acid;

n, n*, o, o*, p and p*, independently of each other, are 0 or 1;

D is $R^1$ or a radical of the formulae V, VI or VII, and
D* is $R^{1*}$ or a radical of the formulae V*, VI* or VII*, $$\begin{array}{c} R^5 \;\; R^9 \\ | \;\;\; | \\ R^1-N-C-CO- \\ | \\ R^{10} \end{array} \quad (V)$$

$$\begin{array}{c} R^{8*} \;\; R^{9*} \\ | \;\;\;\; | \\ R^{1*}-N-\!\!-\!\!-C-CO- \\ | \\ R^{10*} \end{array} \quad (V^*)$$

$$\begin{array}{c} R^{11} \;\; R^9 \\ | \;\;\; | \\ R^1-CH-CH-CO- \end{array} \quad (VI)$$

$$\begin{array}{c} R^{11*} \;\; R^{9*} \\ | \;\;\;\; | \\ R^{1*}-CH-CH-CO- \end{array} \quad (VI^*)$$

$$\begin{array}{c} R^9 \\ | \\ R^1-O-CH-CO- \end{array} \quad (VII)$$

$$\begin{array}{c} R^{9*} \\ | \\ R^{1*}-O-CH-CO- \end{array} \quad (VII^*)$$

and in which $R^1$ and $R^{1*}$, independently of each other, a1) are
hydrogen,
carboxyl,
($C_1$–$C_{18}$)-alkyl, which is optionally unsaturated once or twice and which is optionally substituted by up to 3 identical or different radicals from the group
mercapto,
hydroxyl,
($C_1$–$C_7$)-alkoxy,
carbamoyl,
($C_1$–$C_8$)-alkanoyloxy,
carboxyl,
($C_1$–$C_7$)-alkoxycarbonyl,
F, Cl, Br, I,
amino,
amidino, which can be optionally substituted by one, two or three ($C_1$–$C_8$)-alkyl radicals,
guanidino, which can be optionally substituted by one or two benzyloxycarbonyl radicals or by one, two, three or four ($C_1$–$C_8$)-alkyl radicals,
($C_1$–$C_7$)-alkylamino,
di-($C_1$–$C_7$)-alkylamino,
($C_1$–$C_6$)-alkoxycarbonylamino,
($C_7$–$C_{15}$)-aralkoxycarbonyl,
($C_7$–$C_{15}$)-aralkoxycarbonylamino,
phenyl-($C_1$–$C_4$)-alkoxy,
9-fluorenylmethoxycarbonylamino,
($C_1$–$C_6$)-alkylsulfonyl,
($C_1$–$C_6$)-alkylsulfinyl,
($C_1$–$C_6$)-alkylthio,
hydroxyamino,
hydroxyimino,
sulfamoyl,
sulfo,
carboxamido,
formyl,
hydrazono,
imino,
phenyl,
a radical $CONR^{12}R^{13}$ or $CONR^{12*}R^{13*}$,
by up to six hydroxyl, or
by up to five ($C_1$–$C_8$)-alkanoyloxy;
monocyclic, bicyclic or tricyclic ($C_3$–$C_{18}$)-cycloalkyl,
($C_3$–$C_{18}$)-cycloalkyl-($C_1$–$C_6$)-alkyl
where the cycloalkyl moiety is in each case optionally substituted by one or two identical or different radicals from the group F, Cl, Br, I,
carboxyl,
carbamoyl,
carboxymethoxy,
hydroxyl,
$(C_1-C_7)$-alkoxy,
$(C_1-C_7)$-alkyl,
$(C_1-C_7)$-alkyloxycarbonyl,
amino,
$(C_1-C_6)$-alkylamino-$(C_1-C_6)$-alkyl,
di-$(C_1-C_6)$-alkylamino-$(C_1-C_6)$-alkyl,
amidino,
hydroxyamino,
hydroxyimino,
hydrazono,
imino,
guanidino,
$(C_1-C_6)$-alkoxysulfonyl,
$(C_1-C_6)$-alkoxysulfinyl,
$(C_1-C_6)$-alkoxycarbonylamino,
$(C_6-C_{12})$-aryl-$(C_1-C_4)$-alkoxycarbonylamino,
$(C_1-C_7)$-alkylamino,
di-$(C_1-C_7)$-alkylamino, and
trifluoromethyl;
$(C_6-C_{14})$-aryloxy-$(C_1-C_6)$-alkyl,
$(C_6-C_{14})$-aryl,
$(C_6-C_{14})$-aryl-$(C_1-C_6)$-alkyl, or
$(C_6-C_{14})$-aryl-$(C_3-C_8)$-cycloalkyl, in which the aryl moiety is in each case optionally substituted by one, two or three identical or different radicals from the group
F, Cl, Br, I,
hydroxyl,
mono-, di- or trihydroxy-$(C_1-C_4)$-alkyl,
trifluoromethyl,
formyl,
carboxamido,
mono- or di-$(C_1-C_4)$-alkylaminocarbonyl,
nitro,
$(C_1-C_7)$-alkoxy,
$(C_1-C_7)$-alkyl,
$(C_1-C_7)$-alkoxycarbonyl,
amino,
$(C_1-C_7)$-alkylamino,
di-$(C_1-C_7)$-alkylamino,
carboxyl,
carboxymethoxy,
amino-$(C_1-C_7)$-alkyl,
$(C_1-C_7)$-alkylamino-$(C_1-C_7)$-alkyl,
di-$(C_1-C_7)$-alkylamino-$(C_1-C_7)$-alkyl,
$(C_1-C_7)$-alkoxycarbonylmethoxy,
carbamoyl,
sulfamoyl,
$(C_1-C_7)$-alkoxysulfonyl,
$(C_1-C_8)$-alkylsulfonyl,
sulfo-$(C_1-C_8)$-alkyl,
guanidino-$(C_1-C_8)$-alkyl and
$(C_1-C_6)$-alkoxycarbonylamino;
Het,
Het-$(C_1-C_6)$-alkyl,
Het-$(C_3-C_8)$-cycloalkyl,
Het-$(C_3-C_8)$-cycloalkyl-$(C_1-C_4)$-alkyl,
Het-$(C_3-C_8)$-cycloalkoxy-$(C_1-C_4)$-alkyl,
Het-thio-$(C_1-C_6)$-alkyl,
Het-thio-$(C_3-C_8)$-cycloalkyl,
Het-thio-$(C_3-C_8)$-cycloalkyl-$(C_1-C_4)$-alkyl,
where Het is in each case the radical of a 5- to 7-membered monocyclic or 8- to 10-membered bicyclic ring system which can be benzofuzed, aromatic, partially hydrogenated or completely hydrogenated, which can contain, as heteroelements, one, two, three or four different radicals from the group N, O, S, NO, $SO$, and $SO_2$, which can be substituted by 1 to 6 hydroxyl and which is optionally monosubstituted, disubstituted or trisubstituted as defined for $(C_6-C_{14})$-aryl under a1) and/or by oxo, or are a radical $NR^{12}R^{13}$ or $NR^{12*}R^{13*}$, respectively, or, a2)

are a radical of the formula VIII or VIII*, respectively, $$R1a—W \quad (VIII)$$

$$R1a*—W* \quad (VIII*)$$

in which R1a and R1a* are defined as are $R^1$ and $R^{1*}$, respectively, under a1) and W or W* is —CO—, —CS—, O—CO—, —$SO_2$—, —SO—, —S—, —$NHSO_2$—, —NHCO—, —CH(OH)—, —N(OH)— or —CO—V—, where V is a peptide having from 1 to 10 amino acids;

or in which $R^1$ and $R^{1*}$, independently of each other, form, together with $R^{11}$ or $R^{11*}$, respectively, and the atoms carrying the latter, monocyclic or bicyclic, saturated or partially unsaturated, ring systems having 5–12 ring members which, in addition to carbon, can also contain 1 sulfur atom which can optionally be oxidized to the sulfoxide or sulfone;

a3)

are a glycosyl radical, preferably a glucofuranosyl or glucopyranosyl radical, which is derived from naturally occurring aldotetroses, aldopentoses, aldohexoses, ketopentoses, ketohexoses, deoxyaldoses, aminoaldoses and oligosaccharides and also their stereoisomers;

$R^2$ and $R^{2*}$, independently of each other, are defined as are $R^1$ and $R^{1*}$, respectively, under a1) or a2), or form, together with $R^4$ or $R^{4*}$, respectively, and the atoms carrying the latter, monocyclic or bicyclic, saturated or partially unsaturated, ring systems having from 5 to 12 ring members, or form, together with $R^3$ or $R^{3*}$, respectively, and the atoms carrying the latter, cyclic, saturated or partially unsaturated, ring systems having from 3 to 12 ring members;

$R^3$ and $R^{3*}$, independently of each other, are hydrogen or
$(C_1-C_3)$-alkyl;

$R^4$ and $R^{4*}$, independently of each other, are hydrogen or
$(C_1-C_8)$-alkyl;

$R^5$ is hydrogen,
$(C_1-C_{20})$-alkyl,
$(C_2-C_{20})$-alkenyl or alkynyl,
$(C_7-C_{20})$-arylalkyl or $(C_6-C_{20})$-aryl,
$(C_3-C_8)$-cycloalkyl which can be optionally substituted by different radicals from the group hydroxyl, alkoxy, carboxyl, alkanoyloxy, alkoxycarbonyl, F, Cl, Br, I, amino, alkylamino or dialkylamino;

an equivalent of a pharmaceutically tolerated cation, or is a phosphinate prodrug;

$R^6$ is oxygen or sulfur;

$R^7$ and $R^{7*}$, independently of each other, are hydrogen,
($C_1$–$C_{20}$)-alkyl,
($C_2$–$C_{20}$)-alkenyl or alkynyl, ($C_6$–$C_{20}$)-aryl,
($C_7$–$C_{20}$)-arylalkyl, which can be optionally substituted by different radicals from the group hydroxyl, alkoxy, carboxyl, alkanoyloxy, alkoxycarbonyl, F, Cl, Br, I, amino, alkylamino or dialkylamino,
or, together, can form a ring having 2–6 carbon atoms, $R^8$ and $R^{8*}$, independently of each other, are
hydrogen or
($C_1$–$C_8$)-alkyl, or,
together with $R^9$ or $R^{9*}$, respectively, and the atoms carrying the latter, form monocyclic or bicyclic, saturated or partially unsaturated, ring systems having 5–12 ring members;

$R^9$ and $R^{9*}$
are, independently of each other, defined as are $R^1$ and $R^{1*}$, respectively, under a1), are hydroxyl or ($C_1$–$C_8$)-alkanoyloxy, or form, together with $R^{10}$ or $R^{10*}$, respectively, and the atoms carrying the latter, cyclic, saturated or partially unsaturated, ring systems having from 3 to 12 ring members; or
form, together with $R^{11}$ or $R^{11*}$, respectively, and the atoms carrying the latter, a monocyclic or bicyclic, saturated or partially unsaturated, ring system having 5–12 ring members which, in addition to carbon, can also contain 1 sulfur atom which can optionally be oxidized to the sulfoxide or sulfone; or can contain 1 nitrogen atom, where the ring system can optionally be substituted by amino;

$R^{10}$ and $R^{10*}$, independently of each other, are
hydrogen or
($C_1$–$C_6$)-alkyl;

$R^{11}$ and $R^{11*}$, independently of each other, are
hydrogen,
hydroxyl,
($C_1$–$C_4$)-alkanoyloxy, or
($C_1$–$C_8$)-alkyl;

$R^{12}$, $R^{12*}$, $R^{13}$ and $R^{13*}$, independently of each other, are
hydrogen,
($C_1$–$C_8$)-alkyl which can be substituted by
amino,
($C_1$–$C_4$)-alkylamino,
di-($C_1$–$C_4$)-alkylamino,
mercapto,
carboxyl,
hydroxyl or
($C_1$–$C_4$)-alkoxy,
($C_3$–$C_7$)-cycloalkyl,
($C_1$–$C_4$)-alkoxycarbonyl,
($C_6$–$C_{14}$)-aryl, ($C_6$–$C_{14}$)-aryl-($C_1$–$C_4$)-alkoxycarbonyl which can be substituted in the aryl moiety as described for $R^1$ or $R^{1*}$,
Het or
Het-($C_1$–$C_4$)-alkyl, where Het is defined as described for $R^1$ or $R^{1*}$,
or where $R^{12}$ and $R^{13}$ or $R^{12*}$ and $R^{13*}$, respectively, form, together with the nitrogen atoms carrying them, monocyclic or bicyclic, saturated, partially unsaturated or aromatic ring systems which also contain, as further ring members in addition to carbon, 1 or 2 nitrogen atoms, 1 sulfur atom or 1 oxygen atom, and which can be substituted by ($C_1$–$C_4$)-alkyl,
where
in the above compounds of the formula I, one or more amide groups (—CONH—) of the main chain can be replaced by —$CH_2NR_{14}$—, —$CH_2S$—, —$CH_2O$—, —$OCH_2$—, —$CH_2CH_2$—, —CH=CH— (cis and trans), —$COCH_2$—, —CH(OH)$CH_2$—, —$CH_2SO$—, —$CH_2SO_2$—, —COO—, —P(O)(O$R_{15}$)$CH_2$— and —P(O)(O$R_{15}$)NH—, or even by an amide group having reverse polarity (—NHCO—);
in which $R^{14}$ and $R^{15}$, independently of each other, are hydrogen or
($C_1$–$C_4$)-alkyl;
and the physiologically tolerated salts thereof.

2. A compound of the formula I as claimed in claim 1, wherein the radicals and symbols with and without asterisk are in each case identical.

3. A compound of the formula I as claimed in claim 1, wherein
Q is a radical of the formulae IIa or IIb;
Y is oxygen or sulfur;
A, A*, D, D*, n, n*, o, o*, p and p* are defined as above;
E, E*, F, F*, G and G*, independently of each other, are a natural or unnatural α-amino acid or α-imino acid;
$R^1$ and $R^{1*}$,
independently of each other,
a1*) are
hydrogen;
carboxyl,
($C_1$–$C_{12}$)-alkyl, which is optionally unsaturated once and which is optionally substituted by up to 2 identical or different radicals from the group
hydroxyl,
($C_1$–$C_4$)-alkoxy,
carbamoyl,
($C_1$–$C_8$)-alkanoyloxy,
carboxyl,
($C_1$–$C_4$)-alkoxycarbonyl,
F,
amino,
($C_1$–$C_7$)-alkylamino,
di-($C_1$–$C_7$)-alkylamino,
($C_1$–$C_6$)-alkoxycarbonylamino
benzyloxycarbonyl,
benzyloxycarbonylamino,
9-fluorenylmethoxycarbonylamino,
($C_1$–$C_4$)-alkylsulfonyl,
a radical $CONR^{12}R^{13}$ or $CONR^{12*}R^{13*}$,
by up to three phenyl,
by up to six hydroxyl, or
by up to four ($C_1$–$C_8$)-alkanoyloxy;
monocyclic or bicyclic ($C_3$–$C_{12}$)-cycloalkyl,
($C_3$–$C_{12}$)-cycloalkyl-($C_1$–$C_6$)-alkyl where the cycloalkyl moiety is in each case optionally substituted by one or two identical or different radicals from the group
F,
carboxyl,
hydroxyl,
($C_1$–$C_7$)-alkoxy,
($C_1$–$C_4$)-alkyl,
($C_1$–$C_4$)-alkyloxycarbonyl,
amino,
($C_1$–$C_6$)-alkoxycarbonylamino,
benzyloxycarbonylamino,
($C_1$–$C_4$)-alkylamino, and
di-($C_1$–$C_4$)-alkylamino;
($C_6$–$C_{10}$)-aryloxy-($C_1$–$C_6$)alkyl,
($C_6$–$C_{10}$)-aryl,
($C_6$–$C_{10}$)-aryl-($C_1$–$C_6$)-alkyl, in which the aryl moiety is in each case optionally substituted by one, two or three identical or different radicals from the group F, Cl, Br,
hydroxyl,
hydroxy-$(C_1-C_4)$-alkyl,
carboxamido,
mono- or di-$(C_1-C_4)$-alkylaminocarbonyl,
$(C_1-C_4)$-alkoxy,
$(C_1-C_4)$-alkyl,
$(C_1-C_4)$-alkoxycarbonyl,
amino,
$(C_1-C_4)$-alkylamino,
di-$(C_1-C_4)$-alkylamino,
carboxyl,
carbamoyl,
$(C_1-C_4)$-alkoxycarbonylamino;
Het,
Het-$(C_1-C_6)$-alkyl,
Het-$(C_5-C_6)$-cycloalkyl,
Het-thio-$(C_1-C_4)$-alkyl,
Het-thio-$(C_5-C_6)$-cycloalkyl, where Het is in each case the radical of a 5- to 6-membered monocyclic or 8- to 10-membered bicyclic ring system which can be aromatic, partially hydrogenated or completely hydrogenated, which can contain, as heteroelements, one, two, three or four different radicals from the group N, O, S, NO, SO and $SO_2$, which can be substituted by 1 to 4 hydroxyl, and which is optionally monosubstituted or disubstituted as defined for $(C_6-C_{10})$-aryl under a1) and/or by oxo, or is a radical $NR^{12}R^{13}$ or $NR^{12*}R^{13*}$, respectively, or a2*)
are a radical of the formula VIII or VIII*, respectively, $$R1a—W \quad (VIII)$$

$$R1a*—W* \quad (VIII*)$$

in which R1a and R1a* are defined as are $R^1$ and $R^{1*}$, respectively, under a1*) and W or W* is —CO—, —O—CO—, —$SO_2$—, —SO—, —S—, —NHCO— or —CH (OH)—;
or in which $R^1$ and $R^{1*}$, independently of each other, form, together with $R^{11}$ or $R^{11*}$, respectively, and the atoms carrying the latter, monocyclic, saturated or partially unsaturated, ring systems having 5–8 ring members which, in addition to carbon, can also contain 1 sulfur atom which can optionally be oxidized to the sulfoxide or sulfone;

a3*)
are a glycosyl radical which is defined as in claim 1;

$R^2$ and $R^{2*}$, independently of each other, b1*) are
hydrogen,
carboxyl,
$(C_1-C_{10})$-alkyl which is optionally unsaturated once or twice and which is optionally substituted by up to 3 identical or different radicals from the group
hydroxyl,
$(C_1-C_7)$-alkoxy,
$(C_1-C_7)$-alkylthio,
$(C_1-C_7)$-alkylsulfinyl,
$(C_1-C_7)$-alkylsulfonyl,
$(C_1-C_7)$-alkanoyloxy,
carboxyl,
$(C_1-C_7)$-alkoxycarbonyl,
Cl, Br,
amino,
amidino,
guanidino,
N,N'-di-(benzyloxycarbonyl)guanidino,
carbamoyl,
$(C_7-C_{15})$-aralkoxycarbonyl,
$(C_1-C_5)$-alkoxycarbonylamino,
$(C_7-C_{15})$-aralkoxycarbonylamino, or
9-fluorenylmethoxycarbonylamino;
$(C_3-C_{12})$-cycloalkyl,
$(C_3-C_{12})$-cycloalkyl-$(C_1-C_3)$-alkyl,
$(C_6-C_{14})$-aryl,
$(C_6-C_{14})$-aryl-$(C_1-C_3)$-alkyl, where the aryl moiety is in each case optionally substituted by one, two or three identical or different radicals from the group
F, Cl, Br, I,
hydroxyl,
$(C_1-C_7)$-alkoxy,
$(C_1-C_7)$-alkyl,
$(C_1-C_7)$-alkoxycarbonyl,
amino and
trifluoromethyl; or
Het-$(C_1-C_6)$-alkyl, where Het is the radical of a 5- or 6-membered monocyclic or 9- to 10-membered bicyclic, optionally partially or completely hydrogenated, heteroaromatic compound, having at least 1 C atom, 1–4 N atoms and/or 1–2 S atoms and/or 1–2 O atoms as ring members, which is optionally monosubstituted or disubstituted as described for the aryl moiety in claim 1;

or b2*)
form, together with $R^4$ or $R^{4*}$, respectively, and the atoms carrying the latter, pyrrolidine or piperidine which can in each case also be fused with cyclopentyl, cyclohexyl or phenyl,
or form, together with $R^3$ or $R^{3*}$, respectively, and the atoms carrying the latter, cyclic, saturated or partially unsaturated, ring systems having 3–8 ring members;

$R^3$ and $R^{3*}$, independently of each other, are
hydrogen,
methyl or
ethyl;

$R^4$ and $R^{4*}$, independently of each other, are
hydrogen,
$(C_1-C_4)$-alkyl;

$R^5$ is
hydrogen,
$(C_1-C_6)$-alkyl,
$(C_2-C_6)$-alkenyl or alkynyl,
$(C_7-C_{20})$-arylalkyl, $(C_6-C_{10})$-aryl,
an equivalent of a pharmaceutically tolerated cation or
is glyceryl ester,
1,2-difatty acid glyceryl triester, O-acyloxyalkyl ester or 1-methyl-2-nitroethyl ester, $R^6$ is
oxygen or sulfur;

$R^7$ is defined as described in claim 1, $R^8$ and $R^{8*}$, independently of each other, are
hydrogen,
$(C_1-C_8)$-alkyl or form, together with $R^9$ or $R^{9*}$, respectively, and the atoms carrying the latter, pyrrolidine or piperidine which can in each case be additionally fuzed with cyclopentyl, cyclohexyl or phenyl;

$R^9$ and $R^{9*}$,
independently of each other, are defined as are $R^2$ or $R^{2*}$, respectively, under b1*), or are ($C_1$–$C_8$)-alkanoyloxy, or form, together with $R^{10}$ or $R^{10*}$, respectively, and the atoms carrying the latter, cyclic, saturated or partially unsaturated, ring systems having from 5 to 12 ring members; or form, together with $R^{11}$ or $R^{11*}$, respectively, and the atoms carrying the latter, a monocyclic or bicyclic, saturated or partially unsaturated, ring system having 5–12 ring members which, in addition to carbon, can also contain 1 sulfur atom which can optionally be oxidized to the sulfoxide or sulfone;

$R^{10}$ and $R^{10*}$, independently of each other, are
hydrogen or
($C_1$–$C_4$)-alkyl;

$R^{11}$ and $R^{11*}$,
independently of each other, are
hydrogen,
hydroxyl,
($C_1$–$C_4$)-alkanoyloxy or
($C_1$–$C_4$)-alkyl;

$R^{12}$, $R^{12*}$, $R^{13}$ and $R^{13*}$, independently of each other, are
hydrogen,
($C_1$–$C_8$)-alkyl which can be substituted by
amino,
($C_1$–$C_4$)-alkylamino,
di-($C_1$–$C_4$)-alkylamino,
carboxyl,
hydroxyl or
($C_1$–$C_4$)-alkoxy,
($C_1$–$C_4$)-alkoxycarbonyl,
($C_6$–$C_{10}$)-aryl which can be substituted as described for $R^1$ or $R^{1*}$, respectively
($C_6$–$C_{10}$)-aryl-($C_1$–$C_4$)-alkoxycarbonyl,
Het or
Het-($C_1$–$C_4$)-alkyl, where Het is defined as described for $R^1$ or $R^{1*}$, respectively, where, in the above compounds of the formula I, one or more amide groups (—CONH—) of the main chain can be replaced by a group comprising —$CH_2NR^{14}$—, —$CH_2O$—, —$OCH_2$—, —$CH_2CH_2$—, —$COCH_2$—, —CH(OH)$CH_2$— or —COO—, or else by an amide group having reversed polarity (—NHCO—);

$R^{14}$ is
hydrogen or
($C_1$–$C_4$)-alkyl;

and the physiologically tolerated salts thereof.

4. A compound of the formula I as claimed in claim 1, wherein

Q is a radical of the formulae IIa or IIb;

Y, A, A*, D, D*, n, n*, o and o* are defined as in claim 1, p and p* are 1;

$R^1$ and $R^{1*}$, independently of each other, are
hydrogen,
carboxyl,
($C_1$–$C_{10}$)-alkyl,
($C_3$–$C_8$)-cycloalkyl,
($C_3$–$C_8$)-cycloalkyl-($C_1$–$C_{10}$)-alkyl,
phenyl-($C_1$–$C_8$)-alkyl which can be substituted in the phenyl moiety as described for phenyl in claim 3,
triphenyl-($C_1$–$C_4$)-alkyl,
optionally protected mono- or di-amino-($C_1$–$C_{10}$)-alkyl or amino-($C_6$–$C_{10}$)-aryl-($C_1$–$C_4$)-alkyl or amino-($C_3$–$C_{10}$)-cycloalkyl-($C_1$–$C_4$)-alkyl,
mono-, di-, tri-, tetra-, penta- or hexa-hydroxy-($C_1$–$C_{10}$)-alkyl or -alkanoyl,
($C_1$–$C_4$)-alkoxy-($C_1$–$C_{10}$)-alkyl,
($C_1$–$C_4$)-alkoxycarbonyl-($C_1$–$C_{10}$)-alkyl,
($C_1$–$C_8$)-alkylsulfonyl,
($C_1$–$C_8$)-alkylsulfinyl,
mono-, di- or tri -hydroxy-($C_1$–$C_8$)-alkylsulfonyl,
mono-, di- or tri -hydroxy-($C_1$–$C_8$)-alkylsulfinyl,
mono-, di-, tri- or tetra-($C_1$–$C_8$)-alkanoyloxy-($C_1$–$C_{10}$)-alkyl,
($C_1$–$C_{11}$)-alkanoyl,
optionally protected amino-($C_1$–$C_{11}$)-alkanoyl,
di-($C_1$–$C_7$)-alkylamino-($C_2$–$C_{11}$)-alkanoyl,
($C_1$–$C_9$)-cycloalkylcarbonyl,
amino-substituted ($C_3$–$C_9$)-cycloalkylcarbonyl,
amino-substituted ($C_3$–$C_9$)-cycloalkylsulfonyl,
($C_6$–$C_{10}$)-aryl-($C_2$–$C_7$)-alkanoyl,
($C_6$–$C_{10}$)-aryl-($C_2$–$C_7$)-alkanoyl,
benzoyl, benzenesulfonyl or ($C_6$–$C_{10}$)-aryl-($C_1$–$C_4$)-alkylcarbonyl or -sulfonyl which is optionally substituted by amino, halogen, ($C_1$–$C_7$)-alkyl, ($C_1$–$C_7$)-alkoxy or ($C_1$–$C_7$)-alkoxycarbonyl,
($C_1$–$C_{10}$)-alkoxycarbonyl,
substituted ($C_1$–$C_{10}$)-alkoxycarbonyl,
($C_6$–$C_{14}$)-aryl-($C_1$–$C_6$)-alkoxycarbonyl,
($C_6$–$C_{10}$)-aryl-($C_1$–$C_8$)-alkyl, ($C_3$–$C_{10}$)-cycloalkyl-($C_1$–$C_8$)-alkyl or ($C_1$–$C_{10}$)-alkyl which are substituted by optionally protected amino or hydroxyl,
9-fluorenylmethoxycarbonyl,
ketohexosyl,
ketopentosyl,
deoxyhexoketosyl,
deoxypentoketosyl,
aldohexosyl,
aldopentosyl,
deoxyhexoaldosyl,
deoxypentoaldosyl,
2-amino-2-deoxyhexosyl,
2-acetamido-2-deoxyhexosyl,
lactosyl or
maltosyl where the linked sugars can be present in the pyranose or furanose form,
Het-($C_1$–$C_6$)-alkyl,
Het-carbonyl or -sulfonyl,
Het-($C_1$–$C_6$)-alkylcarbonyl or -sulfonyl,
Het-mercapto-($C_1$–$C_6$)alkylcarbonyl or -sulfonyl, where Het is in each case furyl, thienyl, benzothienyl, benzodioxolanyl, pyrrolyl, imidazolyl, isoxazolyl, thiazolyl, pyrazolyl, triazolyl, pyridyl, pyrimidyl, pyrazinyl, pyridazinyl, triazinyl, pyrrolidyl, piperidyl, piperazinyl, morpholino, thiomorpholino, tetrahydrofuryl, tetrahydropyryl, tetrahydrothienyl, indolyl, quinolyl or isoquinolyl, where these radicals can also be substituted by one or two identical or different radicals from the group ($C_1$–$C_4$)-alkyl, ($C_1$–$C_4$)-alkoxy, ($C_1$–$C_4$)-alkoxycarbonyl, ($C_1$–$C_4$)-alkoxycarbonylamino, hydroxyl, amino, mono- or di-($C_1$–$C_4$)-alkylamino and oxido;

$R^2$ and $R^{2*}$, independently of each other, are
hydrogen,
carboxyl,
($C_1$–$C_8$)-alkyl which is optionally substituted by up to 2 identical or different radicals from the group
hydroxyl,
($C_1$–$C_4$)-alkoxy,
($C_1$–$C_4$)-alkylthio,
($C_1$–$C_4$)-alkylsulfinyl, $(C_1-C_4)$-alkylsulfonyl,
$(C_1-C_4)$-alkanoyloxy,
carboxyl,
$(C_1-C_4)$-alkoxycarbonyl,
amino,
amidino,
guanidino,
N,N'-di-(benzyloxycarbonyl)guanidino,
carbamoyl,
$(C_6-C_{10})$-aryl-$(C_1-C_3)$-alkoxycarbonyl,
$(C_1-C_5)$-alkoxycarbonylamino,
$(C_6-C_{10})$-aryl-$(C_1-C_3)$-alkoxycarbonylamino, or
$(C_3-C_{10})$-cycloalkyl,
$(C_3-C_{10})$-cycloalkyl-$(C_1-C_3)$-alkyl,
$(C_1-C_4)$-alkyl-$(C_3-C_{10})$-cycloalkyl-$(C_1-C_3)$-alkyl,
$(C_6-C_{10})$-aryl,
$(C_6-C_{10})$-aryl-$(C_1-C_3)$-alkyl where the aryl moiety is in each case optionally substituted by one, two or three identical or different radicals from the group
F, Cl, Br,
hydroxyl,
$(C_1-C_4)$-alkoxy,
$(C_1-C_4)$-alkyl,
$(C_1-C_4)$-alkoxycarbonyl and
amino, or
Het-$(C_1-C_4)$-alkyl where Het is defined as in the case of $R^1$ or $R^{1*}$, respectively;

$R^3$ and $R^{3*}$, independently of each other, are,
hydrogen or
methyl;

$R^4$ and $R^{4*}$, independently of each other, are
hydrogen or
methyl;

$R^5$, $R^6$ and $R^7$ are defined as described in claim 3;

$R^8$ and $R^{8*}$, independently of each other, are
hydrogen,
methyl, ethyl or n-propyl, or form, together with $R^9$ or $R^{9*}$, respectively, and the atoms carrying the latter, a 1,2,3,4-tetrahydroisoquinoline or a 2-azabicyclooctane skeleton;

$R^9$ and $R^{9*}$,
independently of each other, are defined as are $R^2$ or $R^{2*}$, respectively, or
are $(C_1-C_8)$-alkanoyloxy or
form, together with $R^{10}$ or $R^{10*}$, respectively, and the atoms carrying the latter, cyclic ring systems having from 5 to 7 ring members;
or form, together with $R^{11}$ or $R^{11*}$, a thiochromane system whose sulfur atom can optionally be oxidized to the sulfone;

$R^{10}$ and $R^{10*}$, independently of each other, are
hydrogen or
methyl;

$R^{11}$ and $R^{11*}$ are defined as described in claim 3;
where,
in the above compounds of the formula 1, one or more amide groups (—CONH—) of the main chain can be replaced as defined in claim 3;

$R^{14}$ is
hydrogen or
methyl;
and the physiologically tolerated salts thereof.

5. A compound of the formula I as claimed in claim 1, wherein

Q is a radical of the formula IIa;

$R^1$ and $R^{1*}$, independently of each other, are
hydrogen,
carboxyl,
$(C_1-C_8)$-alkylsulfonyl,
$(C_1-C_8)$-alkylsulfinyl,
$(C_1-C_8)$-mono-, di- or tri-hydroxyalkylsulfonyl,
hydroxy-$(C_1-C_{10})$-alkanoyl,
mono-, di-, tri- or tetra-hydroxy-$(C_1-C_4)$-alkyl,
$(C_1-C_8)$-alkanoyloxy-$(C_1-C_{10})$-alkyl,
1,2-diacetoxyethyl,
1,2,3-triacetoxypropyl,
$(C_1-C_{11})$-alkanoyl,
amino-$(C_1-C_{11})$-alkanoyl,
N-$(C_1-C_4)$-alkoxycarbonylamino-$(C_1-C_8)$-alkyl,
di-$(C_1-C_7)$-alkylamino-$(C_2-C_{11})$-alkanoyl,
$(C_3-C_9)$-cycloalkylcarbonyl,
amino-$(C_3-C_8)$-cycloalkylcarbonyl,
amino-$(C_3-C_8)$-cycloalkylsulfonyl,
phenyl
triphenyl-$(C_1-C_2)$-alkyl,
$(C_6-C_{10})$-aryl-$(C_1-C_4)$-alkyl,
$(C_6-C_{10})$-aryl-$(C_2-C_7)$-alkanoyl,
$(C_6-C_{10})$-aryloxy-$(C_2-C_7)$-alkanoyl,
benzoyl or -benzenesulfonyl which are optionally substituted by halogen, amino, $(C_1-C_7)$-alkyl, $(C_1-C_7)$-alkoxy or $(C_1-C_7)$-alkoxycarbonyl,
benzylsulfonyl, benzylsulfinyl or benzylthio which are optionally substituted by halogen, amino, $(C_1-C_7)$-alkyl, $(C_1-C_7)$-alkoxy or $(C_1-C_7)$-alkoxycarbonyl,
amino,
$(C_1-C_4)$-alkoxycarbonylamino,
$(C_1-C_{12})$-alkanoyl which is substituted by hydroxyl or amino and optionally by phenyl or cyclohexyl,
$(C_6-C_{10})$-aryl- or $(C_3-C_{10})$-cycloalkyl-$(C_1-C_4)$-alkyl or $(C_1-C_8)$-alkyl which are substituted by optionally protected amino,
$(C_1-C_{10})$-alkoxycarbonyl,
substituted $(C_1-C_{10})$-alkoxycarbonyl,
$(C_6-C_{14})$-aryl-$(C_1-C_6)$-alkoxycarbonyl,
9-fluorenylmethoxycarbonyl,
1-deoxyhexoketosyl or 1-deoxypentoketosyl,
hexosyl or pentosyl,
6-deoxyhexosyl,
aminosugar residues,
lactosyl,
maltosyl,
where the linked sugars can be present in the pyranose or the furanose form,
Het,
Het-carbonyl or Het-sulfonyl,
Het-$(C_1-C_6)$-alkyl,
Het-$(C_1-C_6)$-alkanoyl
Het-$(C_1-C_6)$-alkylsulfonyl,
Het-mercapto-$(C_1-C_3)$-alkylcarbonyl,
where Het is in each case
pyrrolyl,
imidazolyl,
pyridyl,
pyrimidyl,
pyrrolidyl,
piperidyl,
quinolyl,
isoquinolyl or
morpholino,
where the latter can also be substituted by one or two identical or different radicals from the group $(C_1-C_4)$-alkyl, $(C_1-C_4)$-alkoxycarbonyl, $(C_1-C_4)$-alkoxycarbonylamino, hydroxyl, amino or mono- or di-$(C_1-C_4)$-alkylamino;

$R^2$ and $R^{2*}$, independently of each other, are hydrogen,
carboxyl,
methyl, ethyl, isopropyl, n-propyl, n-butyl, isobutyl, sec-butyl, pentyl or hexyl,
cyclohexyl,
cyclopentylmethyl, cyclohexylmethyl or cycloheptylmethyl,
4-methylcyclohexylmethyl,
1-decahydronaphthylmethyl or 2-decahydronaphthylmethyl,
phenyl,
benzyl,
2-phenylethyl,
1-naphthylmethyl or 2-naphthylmethyl,
2-methylbenzyl, 3-methylbenzyl or 4-methylbenzyl,
2,4,6-trimethylbenzyl,
4-tert-butylbenzyl,
4-tert-butoxybenzyl,
4-hydroxybenzyl,
4-methoxybenzyl,
2,4-dimethoxybenzyl,
3,4-dihydroxybenzyl,
3,4-dimethoxybenzyl,
(benzodioxolan-4-yl)methyl,
4-chlorobenzyl,
hydroxymethyl,
1-hydroxyethyl,
2-pyridylmethyl, 3-pyridylmethyl, 4-pyridylmethyl or 2-(4-pyridyl)ethyl,
2-thienylmethyl or 3-thienylmethyl,
2-(2-thienyl)ethyl or 2-(3-thienyl)ethyl,
indol-2-ylmethyl or indol-3-ylmethyl,
(1-methylimidazol-4-yl)methyl,
imidazol-4-ylmethyl or imidazol-1-ylmethyl,
2-thiazolylmethyl,
3-pyrazolylmethyl,
4-pyrimidylmethyl,
2-benzo[b]thienylmethyl or 3-benzo[b]thienylmethyl,
2-furylmethyl,
2-(methylthio)ethyl,
2-(methylsulfinyl)ethyl,
2-(methylsulfonyl)ethyl,
$R^3$, $R^{3*}$, $R^4$, $R^{4*}$, $R^{10}$ and $R^{10*}$ are
hydrogen;
$R^5$ is
hydrogen,
$(C_1-C_6)$-alkyl or
an equivalent of a pharmaceutically tolerated cation;
$R^6$ is
oxygen;
$R^8$ and $R^{8*}$, independently of each other, are
hydrogen or
form, together with $R^9$ or $R^{9*}$, respectively, and the atoms carrying the latter, a 1,2,3,4-tetrahydroisoquinoline or 2-azabicyclooctane skeleton;
$R^9$ and $R^{9*}$, independently of each other, are defined as are $R^2$ or $R^{2*}$, respectively, or are
hydroxyl,
acetoxy,
tert-butoxymethyl,
3-guanidinopropyl,
carbamoylmethyl or carbamoylethyl,
carboxymethyl or carboxyethyl,
mercaptomethyl,
(1-mercapto-1-methyl)ethyl,
aminomethyl, 2-aminoethyl, 3-aminopropyl or 4-aminobutyl,
N,N-dimethylamino,
N,N'-di(benzyloxycarbonyl)guanidinopropyl,
2-benzyloxycarbonylethyl, benzyloxycarbonylmethyl or tert-butylsulfonylmethyl or
4-benzylcarbonylaminobutyl;
$R^{11}$ and $R^{11*}$, independently of each other, are
hydrogen,
hydroxyl or
acetoxy;
where,
in the above compounds of this invention, one or more amide groups (—CONH—) of the main chain can be replaced by —$CH_2NR_{14}$— or —$CH(OH)CH_2$—;
$R^{14}$ is
hydrogen or
methyl;
and the physiologically tolerated salts thereof.

6. A compound of the formula I as claimed in claim 1, wherein
Q is a radical of the formula IIa;
$R^1$ and $R^{1*}$,
independently of each other, are
hydrogen,
carboxyl,
$(C_1-C_8)$-alkylsulfonyl,
$(C_1-C_8)$-mono- or di-hydroxyalkylsulfonyl,
mono-, di- or tri-hydroxy-$(C_1-C_3)$-alkyl,
$(C_1-C_8)$-alkanoyl,
$(C_6-C_{10})$-aryloxy-$(C_1-C_4)$-alkanoyl,
$(C_6-C_{10})$-aryl-$(C_1-C_4)$-alkanoyl,
$(C_1-C_8)$-alkoxycarbonyl
$(C_6-C_{10})$-aryl-$(C_1-C_4)$-alkoxycarbonyl,
9-fluorenylmethoxycarbonyl,
$(C_1-C_4)$-alkanoyloxy-$(C_1-C_6)$-alkyl,
1,2-diacetoxyethyl,
1,2,3-triacetoxypropyl,
phenyl,
triphenylmethyl,
$(C_6-C_{10})$-aryl-$(C_1-C_4)$-alkyl,
benzenesulfonyl which is optionally substituted by halogen, amino, $(C_1-C_4)$-alkyl or methoxy,
benzylsulfonyl, benzylsulfinyl or benzylthio which is optionally substituted by halogen, amino, $(C_1-C_4)$-alkyl or methoxy,
Het,
Het-carbonyl or Het-sulfonyl,
Het-$(C_1-C_4)$-alkylsulfonyl,
Het-$(C_1-C_4)$-alkanoyl,
Het-mercapto-$(C_1-C_3)$-alkylcarbonyl,
where Het is in each case
pyrrolyl,
imidazolyl,
pyridyl,
pyrimidyl,
pyrrolidyl,
piperidyl,
quinolyl,
isoquinolyl or
morpholino,
where this radical can also be substituted by one or two identical or different radicals from the group methyl, amino and $(C_1-C_4)$-alkoxycarbonylamino,
amino-$(C_3-C_6)$-cycloalkylcarbonyl,
$(C_1-C_8)$-alkanoyl which is substituted by hydroxyl and amino and optionally by phenyl or cyclohexyl,
phenyl- or cyclohexyl-$(C_1-C_6)$-alkyl which is substituted by optionally protected amino,
amino,
$(C_1-C_4)$-alkoxycarbonylamino,
benzyloxycarbonylamino,
1-deoxyhexoketosyl or 1-deoxypentoketosyl, hexosyl or pentosyl,
where the linked sugars can be present in the pyranose or the furanose form, $R^2$ and $R^{2*}$, independently of each other, are
hydrogen,
methyl, ethyl, isopropyl, n-propyl, n-butyl, isobutyl, sec-butyl, pentyl or hexyl,
cyclopentylmethyl or cyclohexylmethyl,
4-methylcyclohexylmethyl,
phenyl,
2-phenylethyl,
1-naphthylmethyl or 2-naphthylmethyl,
2-methylbenzyl, 3-methylbenzyl or 4-methylbenzyl,
2,4,6-trimethylbenzyl,
4-tert-butylbenzyl,
4-methoxybenzyl,
3,4-dihydroxybenzyl,
3,4-dimethoxybenzyl,
2-pyridylmethyl, 3-pyridylmethyl, 4-pyridylmethyl, or 2-(4-pyridyl)ethyl, $R^3$, $R^{3*}$, $R^4$, $R^{4*}$, $R^{10}$ and $R^{10*}$ are hydrogen;

$R^5$ and $R^6$ are defined as described in claim 5;

$R^8$ and $R^{8*}$, independently of each other, are
hydrogen or
form, together with $R^9$ or $R^{9*}$, respectively, and the atoms carrying the latter, a 1,2,3,4-tetrahydroisoquinoline or 2-azabicyclooctane skeleton;

$R^9$ and $R^{9*}$,
independently of each other, are defined as $R^9$ and $R^{9*}$, respectively, are described in claim 5;

$R^{11}$ and $R^{11*}$, independently of each other, are
hydrogen;
hydroxyl or
acetoxy;
where,
in the above compounds of this invention, one or more amide groups (—CONH—) of the main chain can be replaced by —CH$_2$NH— or —CH(OH)CH$_2$—;
and the physiologically tolerated salts thereof.

7. A compound of the formula I as claimed in claim 1, wherein
the radicals and symbols with and without an asterisk are in each case identical,
Q is a radical of the formula IIa,
Y is oxygen,
A is a radical of the formula IV in which
E, F or G are Gly, Ala, Val, Leu, Ile, Nva, Nle, Phe, Tyr, Asp or Glu,
and
n+o+p is 0 or 1,
D is $R^1$ or a radical of the formulae V or VI,
$R^1$ is hydrogen, $(C_1-C_6)$-alkylsulfonyl, $(C_6-C_{10})$-aryl-$(C_1-C_2)$-alkyl, triphenylmethyl, $(C_1-C_6)$-alkoxycarbonyl, $(C_6-C_{10})$-aryl-$(C_1-C_2)$-alkanoyl, $(C_6-C_{10})$-aryloxy-$(C_1-C_2)$-alkanoyl, Het-carbonyl or $(C_6-C_{10})$-aryl-$(C_1-C_2)$-alkoxycarbonyl,
$R^2$ is hydrogen, phenyl, benzyl, methyl, ethyl, isopropyl, n-propyl, n-butyl, isobutyl, sec-butyl, pentyl or cyclohexylmethyl,
$R^3$, $R^4$, $R^8$, $R^{10}$ and $R^{11}$ are hydrogen,
$R^5$ is hydrogen or $(C_1-C_6)$-alkyl,
$R^6$ is oxygen, and
$R^9$ is hydrogen, n-propyl, isopropyl, n-butyl, sec-butyl, isobutyl, benzyl, carboxymethyl, carboxyethyl, 1-naphthylmethyl, 2-naphthylmethyl, 2-(methylthio)ethyl, 2-(methylsulfinyl)ethyl, 2-(methylsulfonyl)ethyl, indol-2-ylmethyl or indol-3-ylmethyl,
and the physiologically tolerated salts thereof.

8. A compound of the formula I as claimed in claim 1, wherein
the radicals and symbols with and without an asterisk are in each case identical,
Q is a radical of the formula IIa,
Y is oxygen;
A is a radical of the formula IV, where
E, F or G is Val, Phe, Ile or Asp, and
n+o+p is 0 or 1;
D is $R^1$ or a radical of the formulae V or VI;
$R^1$ is hydrogen, $(C_1-C_6)$-alkylsulfonyl, phenyl-$(C_1-C_2)$-alkyl, triphenylmethyl, $(C_1-C_6)$-alkoxycarbonyl or phenyl-$(C_1-C_2)$-alkoxycarbonyl,
$R^2$ is hydrogen, phenyl, benzyl, methyl, ethyl, isopropyl, n-propyl, n-butyl, isobutyl, sec-butyl, pentyl or cyclohexylmethyl,
$R^3$, $R^4$, $R^8$, $R^{10}$ and $R^{11}$ are hydrogen,
$R^5$ is hydrogen or $(C_1-C_4)$-alkyl,
$R^6$ is oxygen, and
$R^9$ is hydrogen, isopropyl, sec-butyl, benzyl, carboxymethyl, 1-naphthylmethyl, 2-(methylthio)-ethyl or indol-2-ylmethyl,
and the physiologically tolerated salts thereof.

9. A process for preparing a compound of the formula I as claimed in claim 1, wherein a fragment having a terminal carboxyl group, or a reactive derivative of this fragment, is coupled to a corresponding fragment having a free amino group, (a) protective group(s) which has/have, where appropriate, been temporarily introduced to protect further functional groups is/are eliminated, and the compound thus obtained is, where appropriate, converted into its physiologically tolerated salt.

10. A composition containing a compound of the formula I as claimed in claim 1 together with a pharmaceutically acceptable carrier.

* * * * *